US008097760B2

(12) United States Patent
Zhao et al.

(10) Patent No.: US 8,097,760 B2
(45) Date of Patent: Jan. 17, 2012

(54) PREPARATION OF CHIRAL AMIDES AND AMINES

(75) Inventors: Hang Zhao, Westborough, MA (US); Stefan G. Koenig, Shrewsbury, MA (US); Charles P. Vandenbossche, Waltham, MA (US); Surendra Singh, Shrewsbury, MA (US); Harold Scott Wilkinson, Westborough, MA (US); Roger P. Bakale, Malvern, PA (US)

(73) Assignee: Sunovion Pharmacuticals Inc., Marlborough, MA (US)

( * ) Notice: Subject to any disclaimer, the term of this patent is extended or adjusted under 35 U.S.C. 154(b) by 338 days.

(21) Appl. No.: 12/281,819

(22) PCT Filed: Mar. 30, 2007

(86) PCT No.: PCT/US2007/065659
§ 371 (c)(1),
(2), (4) Date: Jan. 30, 2009

(87) PCT Pub. No.: WO2007/115185
PCT Pub. Date: Oct. 11, 2007

(65) Prior Publication Data
US 2009/0149549 A1    Jun. 11, 2009

Related U.S. Application Data

(60) Provisional application No. 60/787,837, filed on Mar. 31, 2006.

(51) Int. Cl.
C07C 321/00 (2006.01)
C07C 323/00 (2006.01)
C07C 381/00 (2006.01)
C07C 211/00 (2006.01)

(52) U.S. Cl. .................................. 564/192; 564/307

(58) Field of Classification Search ............... None
See application file for complete search history.

(56) References Cited

U.S. PATENT DOCUMENTS

| | | | |
|---|---|---|---|
| 4,540,690 A | 9/1985 | Szmuszkovicz | |
| 4,556,676 A | 12/1985 | Welch, Jr. et al. | |
| 4,587,258 A | 5/1986 | Gold et al. | |
| 4,608,382 A * | 8/1986 | Ferrini et al. | 514/341 |
| 4,634,703 A | 1/1987 | Kurtz et al. | |
| 4,687,772 A | 8/1987 | Alderdice | |
| 4,738,709 A | 4/1988 | Nielsen | |
| 4,751,231 A | 6/1988 | Halczenko et al. | |
| 4,981,870 A | 1/1991 | Koe | |
| 5,061,728 A | 10/1991 | Koe | |
| 5,373,018 A | 12/1994 | Cugola et al. | |
| 5,374,649 A | 12/1994 | Cugola et al. | |
| 5,468,749 A | 11/1995 | Gawin et al. | |
| 5,523,278 A | 6/1996 | Wepplo | |
| 5,550,255 A | 8/1996 | Urbach et al. | |
| 5,578,627 A | 11/1996 | Takeda et al. | |
| 5,620,997 A | 4/1997 | Bolton et al. | |
| 5,668,162 A | 9/1997 | Domagala et al. | |
| 5,686,461 A | 11/1997 | Cugola et al. | |
| 5,788,986 A | 8/1998 | Dodman | |
| 5,858,407 A | 1/1999 | Ayer et al. | |
| 5,859,042 A | 1/1999 | Lee et al. | |
| 5,962,496 A | 10/1999 | Cugola et al. | |
| 5,965,591 A | 10/1999 | Kojima et al. | |
| 6,096,771 A | 8/2000 | Kojima et al. | |
| 6,100,289 A | 8/2000 | Cugola et al. | |
| 6,136,824 A | 10/2000 | MacLeod et al. | |
| 6,245,782 B1 | 6/2001 | Serebruany et al. | |
| 6,331,636 B1 | 12/2001 | Romero et al. | |
| 6,372,919 B1 | 4/2002 | Lippa et al. | |
| 6,399,601 B1 | 6/2002 | Du Bois | |
| 6,451,788 B1 | 9/2002 | Horrobin et al. | |
| 6,479,527 B1 | 11/2002 | Barker et al. | |
| 6,506,940 B1 | 1/2003 | Jadav et al. | |
| 6,576,653 B2 | 6/2003 | Du Bois | |
| 6,589,949 B1 | 7/2003 | Moriwaki et al. | |
| 6,603,000 B2 | 8/2003 | Yee et al. | |
| 6,828,460 B2 | 12/2004 | Browning et al. | |
| 6,995,144 B2 | 2/2006 | Ozaki et al. | |
| 7,087,785 B2 | 8/2006 | Jerussi et al. | |
| 7,105,699 B2 | 9/2006 | Jerussi et al. | |
| 7,166,725 B2 | 1/2007 | Fang et al. | |
| 7,226,938 B2 | 6/2007 | Cai et al. | |
| 7,423,179 B2 | 9/2008 | Jerussi et al. | |
| 7,488,747 B2 | 2/2009 | Fang et al. | |
| 7,579,370 B2 | 8/2009 | Heffernan et al. | |
| 7,589,237 B2 | 9/2009 | Jerussi et al. | |
| 7,615,572 B2 | 11/2009 | Fang et al. | |
| 7,790,772 B2 | 9/2010 | Jerussi et al. | |
| 2002/0010198 A1 | 1/2002 | Jerussi et al. | |

(Continued)

FOREIGN PATENT DOCUMENTS

BE         616646       5/1962

(Continued)

OTHER PUBLICATIONS

Abarbri et al., "Les beta-cétonitriles groupes protecteurs de la fonction amine. Préparation d'amino-alcools", Helv. Chim. Acta 1995, 78(1), 109-121.

(Continued)

Primary Examiner — Daniel Sullivan
Assistant Examiner — Jennifer C Sawyer

(57) ABSTRACT

This invention provides a convenient method for converting oximes into enamides. The process does not require the use of metallic reagents. Accordingly, it produces the desired compounds without the concomitant production of a large volume of metallic waste. The enamides are useful precursors to amides and amines. The invention provides a process to convert a prochiral enamide into the corresponding chiral amide. In an exemplary process, a chiral amino center is introduced during hydrogenation through the use of a chiral hydrogenation catalyst. In selected embodiments, the invention provides methods of preparing amides and amines that include the 1,2,3,4-tetrahydro-N-alkyl-1-naphthalenamine or 1,2,3,4-tetrahydro-1-naphthalenamine substructure.

44 Claims, No Drawings

U.S. PATENT DOCUMENTS

| | | |
|---|---|---|
| 2002/0085976 A1 | 7/2002 | Elomari |
| 2002/0123490 A1 | 9/2002 | Howard, Jr. |
| 2002/0183369 A1 | 12/2002 | Du Bois |
| 2003/0078262 A1 | 4/2003 | Taylor |
| 2003/0087803 A1 | 5/2003 | Yatvin et al. |
| 2003/0171440 A1 | 9/2003 | Senanayake et al. |
| 2003/0195361 A1 | 10/2003 | Du Bois |
| 2003/0215523 A1 | 11/2003 | Ozawa et al. |
| 2004/0048878 A1 | 3/2004 | Cai et al. |
| 2004/0077864 A1* | 4/2004 | Kim et al. .................. 546/114 |
| 2004/0092605 A1 | 5/2004 | Jerussi et al. |
| 2004/0106681 A1 | 6/2004 | Rao et al. |
| 2004/0220229 A1 | 11/2004 | Bussolotti et al. |
| 2005/0020645 A1 | 1/2005 | Ohta et al. |
| 2005/0089935 A1 | 4/2005 | Cai et al. |
| 2005/0143434 A1 | 6/2005 | Fang et al. |
| 2005/0143443 A1 | 6/2005 | Fang et al. |
| 2006/0019944 A1 | 1/2006 | Wu et al. |
| 2006/0128993 A1 | 6/2006 | Jerussi et al. |
| 2006/0216799 A1 | 9/2006 | Jerussi et al. |
| 2006/0229286 A1 | 10/2006 | Kakigami et al. |
| 2006/0235002 A1 | 10/2006 | Nagai et al. |
| 2007/0100135 A1 | 5/2007 | Riggs et al. |
| 2007/0142452 A1 | 6/2007 | Banner et al. |
| 2007/0197588 A1 | 8/2007 | Shao et al. |
| 2007/0203111 A1 | 8/2007 | Shao et al. |
| 2007/0282007 A1 | 12/2007 | Tarantino et al. |
| 2008/0004327 A1 | 1/2008 | Heffernan et al. |
| 2008/0004328 A1 | 1/2008 | Dorsey et al. |
| 2008/0058395 A1 | 3/2008 | Heffernan et al. |
| 2008/0262071 A1 | 10/2008 | Dinan et al. |
| 2009/0005456 A1 | 1/2009 | Shao et al. |
| 2009/0099248 A1 | 4/2009 | Heffernan et al. |
| 2010/0016397 A1 | 1/2010 | Fang et al. |
| 2010/0022612 A1 | 1/2010 | Dorsey et al. |
| 2010/0029737 A1 | 2/2010 | Heffernan et al. |
| 2010/0029741 A1 | 2/2010 | Dorsey et al. |
| 2010/0120740 A1 | 5/2010 | Heffernan et al. |
| 2010/0292340 A1 | 11/2010 | Jerussi et al. |

FOREIGN PATENT DOCUMENTS

| | | |
|---|---|---|
| CA | 2066593 A1 | 2/1992 |
| CA | 2410077 A1 | 11/2001 |
| CA | 2474451 A1 | 8/2003 |
| CA | 2498152 A1 | 3/2004 |
| CA | 2498175 A1 | 3/2004 |
| CA | 2565852 A1 | 11/2005 |
| CA | 2566094 A1 | 12/2005 |
| CN | 1106386 A | 8/1995 |
| CN | 1709871 A | 12/2005 |
| CN | 1962656 A | 5/2007 |
| DE | 1124485 A | 3/1962 |
| DE | 3431541 A1 | 3/1986 |
| EP | 0028901 | 5/1981 |
| EP | 0101786 A1 | 3/1984 |
| EP | 0285008 | 10/1988 |
| EP | 0396124 A2 | 11/1990 |
| EP | 0442423 | 8/1991 |
| EP | 0497314 | 8/1992 |
| EP | 1136071 A2 | 9/2001 |
| EP | 1219603 A2 | 7/2002 |
| EP | 1262181 A1 | 12/2002 |
| EP | 1262197 | 12/2002 |
| EP | 1362864 A1 | 11/2003 |
| EP | 1088824 B1 | 1/2004 |
| EP | 1391460 A1 | 2/2004 |
| EP | 1420028 A2 | 5/2004 |
| ES | 2081747 A1 | 3/1996 |
| JP | S54-059269 A | 5/1979 |
| JP | 58 010518 | 1/1983 |
| JP | H01-016786 A | 1/1989 |
| JP | H01-172388 A | 7/1989 |
| JP | 03 246225 | 11/1991 |
| JP | H04-077476 A | 3/1992 |
| JP | 2002 020291 | 1/2002 |
| JP | 2003 335678 | 11/2003 |
| WO | WO 86/00896 A1 | 2/1986 |
| WO | WO 95/17381 A1 | 6/1995 |
| WO | WO 97/31629 | 9/1997 |
| WO | WO 98/42709 A1 | 10/1998 |
| WO | WO 99/10343 A1 | 3/1999 |
| WO | WO 99/18065 * | 4/1999 |
| WO | WO 99/18065 A1 | 4/1999 |
| WO | WO 99/40913 A1 | 8/1999 |
| WO | WO 99/40914 A1 | 8/1999 |
| WO | WO 99/48868 A2 | 9/1999 |
| WO | WO 00/25770 A1 | 5/2000 |
| WO | WO 01/02427 A1 | 1/2001 |
| WO | WO 01/27103 A1 | 4/2001 |
| WO | WO 01/79208 A1 | 10/2001 |
| WO | WO 02/12249 A2 | 2/2002 |
| WO | WO 02/20530 A1 | 3/2002 |
| WO | WO 02/31128 A1 | 4/2002 |
| WO | WO 03/007956 | 1/2003 |
| WO | WO 03/016302 A1 | 2/2003 |
| WO | WO 03/039540 A2 | 5/2003 |
| WO | WO 03/063797 A2 | 8/2003 |
| WO | WO 03/065970 | 8/2003 |
| WO | WO 03/074531 A1 | 9/2003 |
| WO | WO 03/074532 A1 | 9/2003 |
| WO | WO 03/091213 A1 | 11/2003 |
| WO | WO 03/092670 A1 | 11/2003 |
| WO | WO 2004/022537 A2 | 3/2004 |
| WO | WO 2004/024669 | 3/2004 |
| WO | WO 2004/031193 A2 | 4/2004 |
| WO | WO 2004/031194 A2 | 4/2004 |
| WO | WO 2004/039787 A1 | 5/2004 |
| WO | WO 2004/041780 A2 | 5/2004 |
| WO | WO 2004/089470 A2 | 10/2004 |
| WO | WO 2004/113345 A1 | 12/2004 |
| WO | WO 2005/013981 A1 | 2/2005 |
| WO | WO 2005/018637 A1 | 3/2005 |
| WO | WO 2005/020986 A1 | 3/2005 |
| WO | WO 2005/020987 A1 | 3/2005 |
| WO | WO 2005/046575 A2 | 5/2005 |
| WO | WO 2005/066135 A2 | 7/2005 |
| WO | WO 2005/066143 A2 | 7/2005 |
| WO | WO 2005/089753 A2 | 9/2005 |
| WO | WO 2005/123677 A1 | 12/2005 |
| WO | WO 2006/001958 A2 | 1/2006 |
| WO | WO 2006/004040 A1 | 1/2006 |
| WO | WO 2006/021000 A2 | 2/2006 |
| WO | WO 2006/077412 A1 | 7/2006 |
| WO | WO 2007/030589 | 3/2007 |
| WO | WO 2007/039773 A1 | 4/2007 |
| WO | WO 2007/068621 A1 | 6/2007 |
| WO | WO 2007/081542 A2 | 7/2007 |
| WO | WO 2007/081857 A2 | 7/2007 |
| WO | WO 2007/115185 A2 | 10/2007 |
| WO | WO 2007/143267 | 12/2007 |
| WO | WO 2008/005456 A2 | 1/2008 |
| WO | WO 2008/089453 A2 | 7/2008 |
| WO | WO 2008/151156 A1 | 12/2008 |
| WO | WO 2009/020814 A2 | 2/2009 |
| WO | WO 2010/017418 A1 | 2/2010 |
| WO | WO 2010/132521 | 11/2010 |
| WO | WO 2011/069032 | 6/2011 |

OTHER PUBLICATIONS

Aboul-Enein et al., "Synthesis and Antiemetic Profile of N[1-[(diethylamino)methyl]cyclohexyl]amides", Sci. Pharm. 1990, 58(3), 273-280.

Alvaro et al., "Preparation and photolysis of diaryl esters of acetylenedicarboxylic acid", Tetrahedron 1992, 48(16), 3437-3444.

Ando et al., "3-(Arylacetylamino)-N-methylbenzamides: A Novel Class of Selective Anti-Helicobacter pylori Agents", J. Med. Chem. 2001, 44(25), 4468-4474.

Arya et al., "Synthesis of New Heterocycles: Part XV. Synthesis of Novel Cyclic and Acyclic Sulfamides", Indian J. Chem., Sec. B, 1976, 14B(10), 766-769.

Ashton et al., "Nonpeptide angiotensin II antagonists derived from 1H-pyrazole-5-carboxylates and 4-aryl-1H-imidazole-5-carboxylates", J. Med. Chem. 1993, 36(23), 3595-3605.

Associated Press, "FDA mulls drug to slow late-stage Alzheimer's", CNN.com, Sep. 24, 2003, URL: <http://www.cnn.com/2003/HEALTH/conditions/09/24/alzheimers.drug.ap/index.html>.

Aubert et al., "New cyclopenta[b]-pyrroles and -pyridines by reaction of 2-azido- and 2-phosphoranylideneaminocyclopent-1-ene-1-carbaldehydes with aliphatic esters", J. Chem. Soc. Perkin Trans. 1 1989(8), 1369-1373.

Azéma et al., "Efficient approach to acyloxymethyl esters of nalidixic acid and in vitro evaluation as intra-ocular prodrugs", Bioorg. Med. Chem. 2006, 14(8), 2569-2580.

Baba et al., "Structure-Based Design of a Highly Selective Catalytic Site-Directed Inhibitor of Ser/Thr Protein Phosphatase 2B (Calcineurin)", J. Am. Chem. Soc. 2003, 125(32), 9740-9749.

Babu et al., "Simple and facile oxidation of aldehydes to carboxylic acids", Org. Prep. Proced. Int. 1994, 26(1), 123-125.

Bagal et al.,"Radicals from Aldehydes: A Convergent Access to Dienes and δ-Lactones", Synlett 2006(10), 1485-1490.

Balsamini et al., "(E)-3-(2-(N-phenylcarbamoyl)vinyl)pyrrole-2-carboxylic acid derivatives. A novel class of glycine site antagonists", J. Med. Chem. 1998, 41(6), 808-820.

Balsamini et al., "An improved route to cycloalka[b]pyrrole 2-carboxylates", Org. Prep. Proced. Int. 1997, 29(4), 471-473.

Bambury et al., "Trifluoromethylfurans II", J. Heterocycl. Chem. 1970, 7(2), 269-273.

Banekovich et al., "Synthesis and biological activities of novel dexibuprofen tetraacetylriboflavin conjugates", Bioorg. Med. Chem. Lett. 2007, 17(3), 683-687.

Banfi et al., "Synthesis of New Imidazole Derivatives as Potential Inhibitors of Thromboxane Synthetase", J. Heterocycl. Chem. 1990, 27, 215-219.

Bardakos et al., "Enhydrazine, 10. Einige aliphatische Enhydrazone", Chem. Ber. 1975, 108(7), 2161-2170.

Bartlett et al., "Evaluation of alternative approaches for the synthesis of macrocyclic bisindolylmaleimides", Org. Biomol. Chem. 2004, 2(19), 2874-2883.

BASF Corp., "Borane-tetrahydrofuran Complex (BTHF)" Product Bulletin, 2002, pp. 1-14.

Baumes et al., "No. 227.—Recherches sur les enehydrazines. VI.—Condensation de methylhydrazones de cetones sur les esters acetyleniques: synthese de carbomethoxypyrroles", Bull. Soc. Chim. Fr. 1974(5-6), 1147-1150.

Beaumont et al., "Design of Ester Prodrugs to Enhance Oral Absorption of Poorly Permeable Compounds: Challenges to the Discovery Scientist", Curr. Drug Metab. 2003, 4(6), 461-485.

Bedford et al., "Quaternary salts of 2-[(hydroxyimino)methyl]imidazole. 2. Preparation and in vitro and in vivo evaluaton of 1-(alkoxymethyl)-2-[(hydroxyimino)methyl]-3-methylimidazolium halides for reactivation of organophosphorus-inhibited acetylcholinesterases", J. Med. Chem. 1989, 32(2), 493-503.

Benson et al., "Aliphatic β-Chlorovinyl Aldoximes", J. Org. Chem. 1965, 30(4), 1126-1129.

Bergauer et al., "Practical ex-chiral-pool methodology for the synthesis of dopaminergic tetrahydroindoles", Tetrahedron 2004, 60(5), 1197-1204.

Bialer et al., "Pharmacokinetic analysis and antiepileptic activity of tetra-methylcyclopropane analogues of valpromide", Pharm. Res. 1996, 13(2), 284-289.

Biggadike et al., "Selective plasma hydrolysis of glucocorticoid gamma-lactones and cyclic carbonates by the enzyme paraoxonase: an ideal plasma inactivation mechanism." J. Med. Chem. 2000, 43(1), 19-21.

Birkofer et al., "The Use of Silylation in Organic Syntheses", Angew. Chem. Int. Ed. 1965, 4(5), 417-429.

Black, D., "Product Class 13: 1H-Pyrroles" in "Science of Synthesis: Houben-Weyl Methods of Molecular Transformations", vol. 9; Maas, G., ed.; Thieme Medical Publishers: Stuttgart, 2001; pp. 441-552.

Blanchfield et al., "The stability of lipidic analogues of GnRH in plasma and kidney preparations: the stereoselective release of the parent peptide", Bioorg. Med. Chem. Lett. 2005, 15(6), 1609-1612.

Bobbitt et al., "Organic Nitrosonium Salts. II. Stability Studies and Oxidations of Some Indole Derivatives", Heterocycles 1990, 30(2), 1131-1140.

Bobosik et al., "Synthesis of N-Phenylsulfonyl Protected Furo[3,2-b]pyrroles", Collect. Czech. Chem. Commun. 1994, 59(2), 499-502.

Boeshagen et al., "Ueber 3-Acylimino-3H-1.2-benzodithiole", Chem. Ber. 1968, 101(7), 2472-2484.

Borza et al., "Selective NR1/2B N-Methyl-d-aspartate Receptor Antagonists among Indole-2-carboxamides and Benzimidazole-2-carboxamides" J. Med. Chem. 2007, 50(5), 901-914.

Braga et al., "Making crystals from crystals: a green route to crystal engineering and polymorphism", Chem. Commun. 2005(29), 3635-3645.

Bregant et al., "Orthogonally Protected Lanthionines: Synthesis and Use for the Solid-Phase Synthesis of an Analogue of Nisin Ring C", J. Org. Chem. 2005, 70(7), 2430-2438.

Brunner et al., "Asymmetrische Hydrierung von (Z)-α-(Acetylamino)-zimtsäure mit einem Rh/norphos-Katalysator", Angew. Chem. 1979, 91(8), 655-656.

Brunner-Guenat et al., "Esters of L-dopa: structure-hydrolysis relationships and ability to induce circling behaviour in an experimental model of hemiparkinsonism", J. Pharm. Pharmacol. 1995, 47(10), 861-869.

Bueno et al., "Dipeptides as effective prodrugs of the unnatural amino acid (+)-2-aminobicyclo[3.1.0]hexane-2,6-dicarboxylic acid (LY354740), a selective group II metabotropic glutamate receptor agonist." J. Med. Chem. 2005, 48(16), 5305-5320.

Bundgaard et al., "Esters of N,N-disubstituted 2-hydroxyacetamides as a novel highly biolabile prodrug type for carboxylic acid agents", J. Med. Chem 1987, 30(3), 451-454.

Byrn et al., "Solid-State Chemistry of Drugs", 2nd ed.; SSCI, Inc.: West Lafayette, Indiana, 1999; pp. 232-247.

Cai et al., "Synthesis of 2,4,5-Trisubstituted Oxazoles", Synthesis 2005(10), 1569-1571.

Calderon et al., "Novel 1-Phenylcycloalkanecarboxylic Acid Derivatives Are Potent and Selective .sigma.1 Ligands", J. Med. Chem. 1994, 37(15), 2285-2291.

Callis et al., "A Tandem Horner-Emmons Olefination-Conjugate Addition Approach to the Synthesis of 1,5-Disubstituted-6-azabicyclo[3.2.1]octanes Based on the AE Ring Structure of the Norditerpenoid Alkaloid Methyllycaconitine", J. Org. Chem. 1996, 61(14), 4634-4640.

Cartoon et al., "Lithiation reactions of 1-(2'-bromophenyl)pyrrole and related compounds", J. Organomet. Chem. 1981, 212(1), 1-9.

Chakraborty et al., "Synthesis and characterization of Boc-protected 4-amino- and 5-amino-pyrrole-2-carboxylic acid methyl esters", Tetrahedron Lett. 2006, 47(27), 4631-4634.

Chapman et al., "The Analytical Reduction of Porphyrins to Pyrroles", Can. J. Chem. 1971, 49(21), 3544-3564.

Chaubey et al., "Kinetics of the Oxidation of Heterocyclic Aldehydes by Quinolinium Dichromate", Bull. Chem. Soc. Jpn. 2002, 75(10), 2215-2220.

Chen et al., "4,4-Difluoro-4-bora-3a,4a-diaza-s-indacene (BODIPY) Dyes Modified for Extended Conjugation and Restricted Bond Rotations", J. Org. Chem. 2000, 65(10), 2900-2906.

Chen et al., "Studies on the SAR and pharmacophore of milnacipran derivatives as monoamine transporter inhibitors", Bioorg. Med. Chem. Lett. 2008, 18(4), 1346-1349.

Chimichi et al., "New 5-(2-ethenylsubstituted)-3(2H)-furanones with in vitro antiproliferative activity", Tetrahedron 2003, 59(28), 5215-5223.

Cottineau et al., "Synthesis and hypoglycemic evaluation of substituted pyrazole-4-carboxylic acids", Bioorg. Med. Chem. Lett. 2002, 12(16), 2105-2108.

Crane et al., "A Novel Enantioselective Synthetic Route to Omuralide Analogues with the Potential for Species Selectivity in Proteasome Inhibition", Org. Lett. 2001, 3(9), 1395-1397.

Cuevas-Yañez et al., "Rhodium(II) catalyzed intramolecular insertion of carbenoids derived from 2-pyrrolyl and 3-indolyl α-diazo-β-ketoesters and α-diazoketones", Tetrahedron 2004, 60(7), 1505-1511.

Cyranski et al., "Aromaticity of dihetero analogues of pentalene dianion. X-Ray and ab initio studies of eight methyl furo[3,2-b]pyrrole-5-carboxylate derivatives and five methyl furo[2,3-b]pyrrole-5-carboxylate derivatives", Tetrahedon 2001, 57(42), 8867-8873.

Damaslo, A. R., "Alzheimer's Disease and Related Dementias" in "Cecil Textbook of Medicine", 20th ed., vol. 2; W.B. Saunders Co.: Philadelphia, 1996; pp. 1992-1996.

Dandarova et al., "13C NMR spectra of some substituted furo[3,2-b]pyrroles", Magn. Reson. Chem. 1990, 28(9), 830-831.
Das et al., "Synthesis of some N-substituted carbazoles and their larvicidal studies", J. Indian Chem. Soc. 2005, 82, 158-160.
Database Beilstein, Beilstein Institute for Organic Chemistry, Frankfurt-Main, DE; Database Accession No. BRN: 10196160 Abstract; and Eur. J. Org. Chem. 2005(21), 4670-4679.
Database Beilstein, Beilstein Institute for Organic Chemistry, Frankfurt-Main, DE; Database Accession No. BRN: 1074598 Abstract; and Can. J. Chem. 1978, 56(10), 1429-1434.
Database Beilstein, Beilstein Institute for Organic Chemistry, Frankfurt-Main, DE; Database Accession No. BRN: 4185621 Abstract; and Collect. Czech. Chem. Commun. 1986, 51(1), 106-111.
Database Beilstein, Beilstein Institute for Organic Chemistry, Frankfurt-Main, DE; Database Accession No. BRN: 4429388 Abstract; and Collect. Czech. Chem. Commun. 1984, 49(1), 65-70.
Database Beilstein, Beilstein Institute for Organic Chemistry, Frankfurt-Main, DE; Database Accession No. BRN: 7812555 Abstract; and Collect. Czech. Chem. Commun. 1997, 62(10), 1612-1622.
Database CAPLUS on STN, Acc. No. 1977:83511, Koe, J. Pharmacol. Exp. Ther. 1976, 199(3), 649-661. [abstract].
De Luca et al., "A New, Simple Procedure for the Synthesis of Formyl Amides", Synlett 2004(14), 2570-2572.
Denmark et al., "Chiral fluoro ketones for catalytic asymmetric epoxidation of alkenes with oxone", J. Org. Chem. 2002, 67(10), 3479-3486.
Denmark et al., "Organocerium additions to SAMP-hydrazones: general synthesis of chiral amines", J. Am. Chem. Soc. 1987, 109(7), 2224-2225.
Dhanak et al., "Studies in the protection of pyrrole and indole derivatives", J. Chem. Soc., Perkin Trans. 1, 1986, 2181-2186.
Durrer et al., "Structure-metabolism relationships in the hydrolysis of nicotinate esters by rat liver and brain subcellular fractions", Pharm. Res. 1991, 8(7), 832-839.
Elghamry, "Synthesis of ethyl pyrrole-2-carboxylates: a regioselective cyclization of enaminones under knorr-type conditions", Synth. Commun. 2002, 32(6), 897-902.
Eliel, "Infelicitous stereochemical nomenclature", Chirality 1997, 9(5-6), 428-430.
El-Nagger et al., "Synthesis and Biological Activity of Some New Aminoacylcarbazole Derivatives. Part I", J. Heterocycl. Chem. 1982, 19, 1025-1028.
English et al., "Orally effective acid prodrugs of the beta-lactamase inhibitor sulbactam", J. Med. Chem. 1990, 33(1), 344-347.
Eras et al., "Reactivity of thienopyrroles. Synthesis of isomeric nitro and bromothienopyrroles", J. Heterocycl. Chem. 1984, 21(1), 215-217.
Estep, "An Efficient Synthesis of 4-Hydroxy-1H-indole-2-carbonitrile and Its Conversion to DPI 201-106", Synth. Commun. 1995, 25(4), 507-514.
Fagan et al., "A new approach to the core of roseophilin", Tetrahedron Lett. 1999, 40(33), 6117-6120.
Ferguson et al., "N-Acetyl-5,6-dihydrofuro[3,2-b]pyrid-2-one, C9H9NO3", Cryst. Struct. Comm. 1976, 5, 911-914.
Fischer et al., "On Benzisothiazolones: A Series with a Wide Range of Bacteriostatic and Fungistatic Activity", Arzneimittel-Forschung 1964, 14(12), 1301-1306.
Fischer et al., "Synthese einiger Pyrrole und ihre Umsetzungen", Justus Liebigs Ann. Chem. 1932, 492(1), 128-155.
Fischer et al., "Synthesen der Opso- und Hämopyrrolcarbonsäure. Neue Synthese von Koproporphyrin. II", Justus Liebigs Ann. Chem. 1928, 462(1), 240-250.
Fischer et al., "Synthesen von Koproporphyrin I und II, sowie Mesoporphyrin II, V und XII", Justus Liebigs Ann. Chem. 1928, 466(1), 147-178.
Fisera et al., "Correlation of Kinetic Data of 1,3-Dipolar Cycloadditions of C-Benzoyl-N-phenylnitrones with the Homo Energies of Furan Derivatives", Collect. Czech. Chem. Commun. 1981, 46, 1504-1512.
Fisera et al., "Cycloadditions of C-Benzoyl-N-phenylnitrone with Furocondensed Derivatives", Collect. Czech. Chem. Commun. 1981, 46, 2421-2427.
Flaugh et al., "Synthesis of porphyrins. Deoxophylloerythroetioporphyrin", J. Am. Chem. Soc. 1968, 90(24), 6877-6879.
Foucaud et al., "The [1+4] cycloaddition of isocyanides with 1-aryl-2-nitro-1-propenes. Methyl 2-nitro-3-arylpropenoates and methyl 2-nitro-2,4-pentadienoates. Synthesis of 1-hydroxyindoles and 1-hydroxypyrroles", J. Org. Chem. 1983, 48(21), 3639-3644.
Fraga-Dubreuil et al., "Grafted ionic liquid-phase-supported synthesis of small organic molecules", Tetrahedron Lett. 2001, 42(35), 6097-6100.
Franciò et al., "Asymmetric Catalysis with Chiral Phosphane/Phosphoramidite Ligands Derived from Quinoline (QUINAPHOS)", Angew. Chem. Int. Ed. 2000, 39(8), 1428-1430.
Frisell et al., "Flavoenzyme Catalysis. Substrate-Competitive Inhibition of D-Amino Acid Oxidase", J. Biol. Chem. 1956, 223, 75-83.
Fu et al., "Design and synthesis of novel bis(I-amino acid) ester prodrugs of 9-[2-(phosphonomethoxy)ethyl]adenine (PMEA) with improved anti-HBV activity", Bioorg. Med. Chem. Lett. 2007, 17(2), 465-470.
Fukuda et al., "Tensidols, New Potentiators of Antifungal Miconazole Activity, Produced by Aspergillus niger FKI-2342", J. Antibiot. 2006, 59(8), 480-485.
Gabbutt et al., "A Facile Synthesis of Some Benzothiopyrano[4,3-b]pyrroles", J. Chem. Res. (S) 1997(3), 102-103.
Gale et al., "Preparation and Reactions of 5-Carbethoxythieno[3,2-b]pyrrole and Some of Its Derivatives", J. Org. Chem. 1964, 29(8), 2160-2165.
Garg et al., "Development of an Enantiodivergent Strategy for the Total Synthesis of (+)- and (−)-Dragmacidin F from a Single Enantiomer of Quinic Acid", J. Am. Chem. Soc. 2005, 127(16), 5970-5978.
Gelas-Mialhe et al., "Photochemical heterocyclization of functionalized dienamines", J. Org. Chem. 1987, 52(24), 5395-5400.
Gelas-Mialhe et al., "Réactivité des N-vinylaziridines fonctionnalisées. Synthèse de dérivés des α,β-déhydro α-amino acides", Can. J. Chem. 1982, 60(22), 2830-2851.
Geraldine et al., "How an increase in the carbon chain length of the ester moiety affects the stability of a homologous series of oxprenolol esters in the presence of biological enzymes", J. Pharm. Sci. 1998, 87(7), 880-885.
Gross et al., "Direct observation of 1-azafulven-6-one and annelated derivatives", J. Chem. Soc., Chem. Commun. 1982(6), 360-361.
Grygorenko et al., "Stereoselective synthesis of 2,4-methanoproline homologues", Tetrahedron Asymmetry 2006, 17(2), 252-258.
Guan et al., "Design and synthesis of aminopropyl tetrahydroindole-based indolin-2-ones as selective and potent inhibitors of Src and Yes tyrosine kinase", Bioorg. Med. Chem. Lett. 2004, 14(1), 187-190.
Haginoya et al., "Synthesis and conformational analysis of a non-amidine factor Xa inhibitor that incorporates 5-methyl-4,5,6,7-tetrahydrothiazolo[5,4-c]pyridine as S4 binding element", J. Med. Chem. 2004, 47(21), 5167-5182.
Haj-Yehia et al., "Pharmacokinetic analysis of the structural requirements for forming "stable" analogues of valpromide", Pharm. Res. 1992, 9(8), 1058-1063.
Haj-Yehia et al., "Structure-pharmacokinetic relationships in a series of valpromide derivatives with antiepileptic activity", Pharm. Res. 1989, 6(8), 683-689.
Harada et al., "A Simple Preparation of Chloromethyl Esters of the Blocked Amino Acids", Synth. Commun. 1994, 24(6), 767-772.
Harrak et al.,"PtCl2-Catalyzed Cycloisomerizations of 5-En-1-yn-3-ol Systems", J. Am. Chem. Soc. 2004, 126(28), 8656-8657.
Harrison et al., "Cyclopenta[b]indoles. Part 2. Model studies towards the tremorgenic mycotoxins", J. Chem. Soc. Perkin Trans. 1 1995(9), 1131-1136.
Harwood et al., "Tandem generation and intramolecular trapping of chiral stabilised azomethine ylids with alkyne dipolarophiles", Tetrahedron Lett. 1993, 34(41), 6603-6606.
Hauptmann et al., "Beiträge zum Reaktionsverhalten von 2-Aminovinylcarbonylverbindungen", Journal für Praktische Chemie 1972, 314(2), 353-364.
Hauptmann et al., "Eine neue Synthese substituierter Thiophene und Pyrrole", Tetrahedron Lett. 1968, 9(11), 1317-1319.

Hemetsberger et al., "Synthese und Thermolyse von α-Azidoacrylestern", Monatsh. Chem. 1972, 103(1), 194-204.

Hillenweck et al., "Chlorothalonil Biotransformation by Gastrointestinal Microflora: In Vitro Comparative Approach in Rat, Dog, and Human", Pestic. Biochem. Physiol. 1997, 58(1), 34-48.

Hilton et al., "Observations on the reactivity of thiyl radicals derived from 3,6-epidithiodiketopiperazine-2,5-diones and related congeners", Bioorg. Med. Chem. Lett. 2005, 15(9), 2239-2242.

Hoffman, R. V., "Organic Chemistry: An Intermediate Text, Second Edition"; Wiley: Hoboken, 2004; pp. 124 and 138-144.

Holmes et al., "Reactions of N-Benzylthieno[3,2-b]pyrrole. I. Metalation and an Electrophilic Substitution", J. Org. Chem. 1964, 29(8), 2155-2160.

Hori, M., "Syntheses of Analgesics. XIV. Aminocyclohexane Derivatives. 8.", Yakugaku Zasshi 1958, 78, 11-14.

Howarth et al., "Pyrroles and related compounds. Part XXVI. Pyrrole beta-keto-esters", J. Chem. Soc. Perkin Trans. 1 1974, 490-501.

Hu et al., "Synthesis of a Porphyrin with Fused Five- and Seven-membered Exocyclic Rings from a Cross-conjugated Tetracydic Dipyrrole", Synlett 1994(11), 909-910.

Ikegami et al., "Synthesis and pharmacological activity of O-(5-isoxazolyl)-L-serine", Chem. Pharm. Bull. 2000, 48(2), 278-280.

Ilyin et al., "Synthesis of Annelated Azaheterocycles Containing a 5-Carbamoylpyrazin-3-one Fragment by a Modification of the Four-Component Ugi Reaction", Eur. J. Org. Chem. 2005(21), 4670-4679.

Ingram et al., "Investigation of enzyme activity by SERRS using poly-functionalised benzotriazole derivatives as enzyme substrates", Org. Biomol. Chem. 2006, 4(15), 2869-2873.

Inukai et al., "ortho-Disubstituted F-Benzenes. III. Preparation of (F-Benzo)heterocyclic Compounds from F-Benzoic Acid and F-Phenol, and the Reactions of Some Intermediary F-Benzoyl- and F-Phenoxy Compounds", Bull. Chem. Soc. Jpn. 1981, 54(11), 3447-3452.

Iranpoor et al., "A Rapid and Facile Conversion of Primary Amides and Aldoximes to Nitriles and Ketoximes to Amides with Triphenylphosphine and N-Chlorosuccinimide", Synth. Commun. 2002, 32(16), 2535-2541.

Isoherranen et al., "New CNS-active drugs which are second-generation valproic acid: can they lead to the development of a magic bullet?", Curr. Opin. Neurol. 2003, 16(2), 203-211.

Jacob et al., "gamma-Aminobutyric acid esters. 2. Synthesis, brain uptake, and pharmacological properties of lipid esters of gamma-aminobutyric acid", J. Med. Chem. 1985, 28(1), 106-110.

Java et al., "Chimie Organique.—Synthese de selenolo, furo et pyrrolopyrroles", C. R. Acad. Sc. Paris 1975, 281 Serie C (19), 793-795.

Jolicoeur et al., "Pyrrole protection", Tetrahedron 2006, 62(50), 11531-11563.

Katritzky et al., "Efficient Conversion of Carboxylic Acids into N-Acylbenzotriazoles", Synthesis 2003(18), 2795-2798.

Katritzky et al., "Novel Synthesis of Bicycles with Fused Pyrrole, Indole, Oxazole, and Imidazole Rings", J. Org. Chem. 2004, 69(26), 9313-9315.

Katritzky et al., "Regiospecific C-Acylation of Pyrroles and Indoles Using N-Acylbenzotriazoles", J. Org. Chem. 2003, 68(14), 5720-5723.

Katterle et al., "A Heck-Type Coupling for the Synthesis of Novel Bridged Metallochlorin-Fullerene C60 Dyads", European J. Org. Chem. 2006(2), 414-422.

Keener et al., "Synthesis of 6-substituted thieno[3,2-b]pyrroles", J. Org. Chem. 1968, 33(4), 1355-1359.

Kesel, "Synthesis of Novel Test Compounds for Antiviral Chemotherapy of Severe Acute Respiratory Syndrome (SARS)", Curr. Med. Chem. 2005, 12(18), 2095-2162.

Khanna et al., "Evaluation of glycolamide esters of indomethacin as potential cyclooxygenase-2 (COX-2) inhibitors", Bioorg. Med. Chem. 2006, 14(14), 4820-4833.

Kittredge et al., "alpha-Helical Polypeptide Films Grown From Sulfide or Thiol Linkers on Gold Surfaces", Helv. Chim. Acta 2002, 85(3), 788-798.

Kleinspehn et al., "The Synthesis of Some β, β-Dipyrrylpropionic Esters", J. Am. Chem. Soc. 1954, 76(22), 5641-5646.

Koe, "Molecular geometry of inhibitors of the uptake of catecholamines and serotonin in synaptosomal preparations of rat brain", J. Pharmacol. Exp. Ther. 1976, 199(3), 649-661.

Kralovicova et al., "Electrophilic Substitution Reactions of Furo[3,2-b]pyrrole Derivatives", Collect. Czech. Chem. Commun. 1986, 51(1), 106-111.

Krayushkin et al., "Synthesis of Photochromic 1,2-Dihetarylethene Using Regioselective Acylation of Thienopyrroles", Org. Lett. 2002, 4(22), 3879-3881.

Kren et al., "Clustered ergot alkaloids modulate cell-mediated cytotoxicity", Bioorg. Med. Chem. 2002, 10(2), 415-424.

Krutosikova et al., "Addition and Cycloaddition Reactions of Furo[3,2-b]pyrroles and Their Benzo[b] Analogues: An NMR Study of Structure of Products", Collect. Czech. Chem. Commun. 1988, 53(5), 1770-1778.

Krutosikova et al., "Effect of microwave irradiation on reaction of furo[3,2-b]pyrrole and furo[2,3-b]pyrrole-2-carbaldehydes with some active methylene compounds", ARKIVOC 2000(iii), 409-420.

Krutosikova et al., "Reactions of Ethyl 2-(4-chlorophenyl)-4H-furo[3,2-b]pyrrole-5-carboxylate", Collect. Czech. Chem. Commun. 1980, 45(III), 2949-2957.

Krutosikova et al., "Reactions of furo[3,2-b]pyrroles and their benzo[b] analogues", Chem. Papers 1988, 42(1), 89-95.

Krutosikova et al., "Reactions of Methyl 2-Formylfuro[3,2-b]pyrrole-5-carboxylates", Chem. Papers 1996, 50(2), 72-76.

Krutosikova et al., "Substituted 4-Benzylfuro[3,2-b]pyrroles", Collect. Czech. Chem. Commun. 1992, 57(5), 1487-1494.

Krutosikova et al., "Substituted Vinyl Azides in the Synthesis of Condensed Nitrogen Heterocycles", Chem. Papers 1994, 48(4), 268-273.

Krutosikova et al., "Synthesis and Reactions of 4-Oxiranylmethylfuro[3,2-b]pyrroles and Their Benzo Derivatives", Chemistry of Heterocyclic Compounds 2001, 37(12), 1511-1517.

Krutosikova et al., "Synthesis and Reactions of 8-Hydrazinofuro[2',3':4,5]pyrrolo-[1,2-d][1,2,4]triazines", Collect. Czech. Chem. Commun. 1997, 62(10), 1612-1622.

Krutosikova et al., "Synthesis and Reactions of Furo[2,3-b]pyrroles", Molecules 1997, 2(4), 69-79.

Krutosikova et al., "Synthesis and Reactions of Furocondensed Derivatives", Collect. Czech. Chem. Commun. 1984, 49(1), 65-70.

Krutosikova et al., "Synthesis and Reactions of Substituted Furo[3,2-b]pyrrole Derivatives", Collect. Czech. Chem. Commun. 1981, 46, 2564-2572.

Kukolja et al., "Orally absorbable cephalosporin antibiotics. 2. Structure-activity studies of bicyclic glycine derivatives of 7-aminodeacetoxycephalosporanic acid", J. Med. Chem. 1985, 28(12), 1896-1903.

Kumar et al., "Synthesis and biological evaluation of thiophene [3,2-b] pyrrole derivatives as potential anti-inflammatory agents", Bioorg. Med. Chem. 2004, 12(5), 1221-1230.

Kuo et al., "G-protein coupled receptors: SAR analyses of neurotransmitters and antagonists", J. Clin. Pharm. Ther. 2004, 29(3), 279-298.

Lamboley et al., "Synthesis and Properties of Conformationally Constrained Analogues of Floral-Type Odorants", Helv. Chim. Acta 2004, 87(7), 1767-1793.

Lash et al., "Influence of carbocyclic rings on porphyrin cyclizations: synthesis of geochemically significant cycloalkanoporphyrins", Energy Fuels 1990, 4(6), 668-674.

Lash et al., "Normal and Abnormal Heme Biosynthesis. 2.1 Synthesis and Metabolism of Type-III Pentacarboxylic Porphyrinogens: Further Experimental Evidence for the Enzymic Clockwise Decarboxylation of Uroporphyrinogen-III", J. Org. Chem. 1999, 64(2), 478-487.

Lash et al., "Porphyrins with exocyclic rings. 1. Chemistry of 4,5,6,7-tetrahydro-1H-indoles: synthesis of acetoxy derivatives, dihydroindoles, and novel porphyrins with four exocyclic rings", J. Org. Chem. 1992, 57(18), 4809-4820.

Lash et al., "Porphyrins with exocyclic rings. Part 3. A reassessment on the utility of cyclopenta[b]pyrroles in the synthesis of porphyrin molecular fossils. Preparation of three type II porphyrins related to deoxophylloerythroetioporphyrin (DPEP)", Tetrahedron 1993, 49(20), 4159-4172.

Lash et al., "Recent advances in the synthesis of porphyrins with five-membered exocyclic rings", Energy Fuels 1993, 7(2), 172-178.

Law et al., "The synthesis and chemistry of azolenines. Part 2. A general synthesis of pyrrole-2-carboxylic acid derivatives by the reaction of 2H-azirines with enamines, and the crystal and molecular structure of ethyl 3-phenyl-4,5,6,7-tetrahydroindole-2-carboxylate", J. Chem. Soc. Perkin Trans. 1 1984, 111-118.

Layzer, R. B., "Section Five—Degenerative Diseases of the Nervous System" in "Cecil Textbook of Medicine", 20th ed., vol. 2; W.B. Saunders Co.: Philadelphia, 1996; pp. 2050-2057.

Lee at al., "Amphiphilic amino acid copolymers as stabilizers for the preparation of nanocrystal dispersion", Eur. J. Pharm. Sci. 2005, 24(5), 441-449.

Lee et al., "An Effective and Convenient Esterification of Cephalosporin Derivatives by Using Quarternary Ammonium Salts as Catalysts", Synth. Commun. 1998, 28(23), 4345-4354.

Lerche et al., "Umsetzungen mit Monohydrazonen von Dicarbonylverbindungen, V: Umsetzungen von Hydrazonoethylidenammonium-Salzen and Hydrazonoaldehyden mit Grignard-Verbindungen", Chem. Ber. 1978, 111(3), 1195-1209.

Li et al., "Synthesis of deoxophylloerythroetioporphyrin (DPEP) and three ring homologs by an improved b-bilene methodology", Tetrahedron Lett. 1998, 39(47), 8571-8574.

Liederer et al., "Enzymes involved in the bioconversion of ester-based prodrugs", J. Pharm. Sci. 2006, 95(6), 1177-1195.

Liederer et al., "Stability of oxymethyl-modified coumarinic acid cyclic prodrugs of diastereomeric opioid peptides in biological media from various animal species including human", J. Pharm. Sci. 2005, 94(10), 2198-2206.

Liu et al., "Facile construction of the pentacyclic framework of subincanadine B. Synthesis of 20-deethylenylated subincanadine B and 19,20-dihydrosubincanadine B", Org. Lett. 2006, 8(1), 115-118.

Liu et al., "Indole-5-phenylcarbamate derivatives as human non-pancreatic secretory phospholipase A2 inhibitor", Bioorg. Med. Chem. Lett. 2005, 15(20), 4540-4542.

Liu et al., "The synthesis of camostat intermediate", Huaxue Shiji, 2006, 28(6), 371-372.

Ma et al., "Hydrolysis of angiotensin II receptor blocker prodrug olmesartan medoxomil by human serum albumin and identification of its catalytic active sites", Drug Metab. Dispos. 2005, 33(12), 1911-1919.

Majumdar et al., "α-(1H-Imidazol-1-yl)alkyl (IMIDA) carboxylic acid esters as prodrugs of carboxylic acid containing drugs", Tetrahedron Lett. 2007, 48(26), 4609-4611.

Mal et al., "Regioselective synthesis of 1-hydroxycarbazoles via anionic [4+2] cycloaddition of furoindolones: a short synthesis of murrayafoline-A", Tetrahedron Lett. 2006, 47(7), 1071-1075.

Mamber et al., "Tubulin polymerization by paclitaxel (taxol) phosphate prodrugs after metabolic activation with alkaline phosphatase", J. Pharmacol. Exp. Ther. 1995, 274(2), 877-883.

Mandel et al., "Neuroprotective Strategies in Parkinson's Disease: An Update on Progress", CNS Drugs 2003, 17(10), 729-762.

Marrel et al., "L-Dopa esters as potential prodrugs 1. Physicochemical properties", Eur. J. Med. Chem. 1985, 20(5), 459-465.

Marrel et al., "L-Dopa esters as potential prodrugs 2. Chemical and enzymatic-hydrolysis", Eur. J. Med. Chem. 1985, 20(5), 467-470.

Martin et al., "Das Diazo-chinon von PQQ als mögliches Reagenz für die Kartierung von Chinoproteinen mittels Photoaffinitätsmarkierung", Helv. Chim. Acta 1993, 76(4), 1674-1677.

Martin et al., "Do structurally similar molecules have similar biological activity?", J. Med. Chem. 2002, 45(19), 4350-4358.

McConnaughie et al., "Novel Acridine-Triazenes as Prototype Combilexins: Synthesis, DNA Binding, and Biological Activity" J. Med. Chem. 1995, 38(18), 3488-3501.

McLaughlin, "Suzuki-Miyaura Cross-Coupling of Benzylic Phosphates with Arylboronic Acids", Org. Lett. 2005, 7(22), 4875-4878.

Medforth et al., "Nonplanar distortion modes for highly substituted porphyrins", J. Am. Chem. Soc. 1992, 114(25), 9859-9869.

Meltzer et al., "The synthesis of bivalent 2β-carbomethoxy-3β-(3,4-dichlorophenyl)-8-heterobicyclo[3.2.1]octanes as probes for proximal binding sites on the dopamine and serotonin transporters", Bioorg. Med. Chem. 2008, 16(4), 1832-1841.

Mergen et al., "Antiepileptic activity of 1,3-dihexadecanoylamino-2-valproyl-propan-2-ol, a prodrug of valproic acid endowed with a tropism for the central nervous system", J. Pharm. Pharmacol. 1991, 43(11), 815-816.

Merisor et al., "Synthesis of New Derivatives in the Izoxazole Class with Potential Antimicrobial Activity", Rev. Chim. (Bucharest, Romania) 2001, 52(4), 206-209.

Miao et al., "Benzamide derivatives as blockers of Kv1.3 ion channel", Bioorg. Med. Chem. Lett. 2003, 13(6), 1161-1164.

Mikhaleva et al., "Expedient synthesis of 1-vinylpyrrole-2-carbaldehydes", Tetrahedron Lett. 2006, 47(22), 3693-3696.

Miki et al., "Synthesis of 3-Methoxyellipticine and Ellipticine by Friedel-Crafts Reaction of Indole-2,3-dicarboxylic Anhydride and Selective Demethylation", Heterocycles 2005, 65(11), 2693-2703.

Milkiewicz et al., "Synthesis of a novel series of tetra-substituted furan[3,2-b]pyrroles", Tetrahedron Lett. 2003, 44(22), 4257-4260.

Mishra et al., "Synthesis, characterization and pharmacological evaluation of amide prodrugs of ketorolac", Eur. J. Med. Chem. 2008, 43(11), 2464-2472.

Mokhallalati et al., "A single-pot synthesis of 1,1,2-trisubstituted 1,2-dihydronaphthalenes in high enantiomeric purity", Tetrahedron Lett. 1994, 35(25), 4267-4270.

Montero et al., "Solid-Phase Combinatorial Synthesis of Peptide-Biphenyl Hybrids as Calpain Inhibitors", Org. Lett. 2004, 6(22), 4089-4092.

Morgan et al., "Synthesis of hydrocarbon-strapped porphyrins containing quinone and phenolic groups", J. Org. Chem. 1987, 52(24), 5364-5374.

Morissette et al., "High-throughput crystallization: polymorphs, salts, co-crystals and solvates of pharmaceutical solids", Adv. Drug Deliv. Rev. 2004, 56(3), 275-300.

Mork et al., "Stereoselective enzymatic hydrolysis of various ester prodrugs of ibuprofen and flurbiprofen in human plasma", Pharm. Res. 1992, 9(4), 492-496.

Muchowski et al., "Protecting groups for the pyrrole and indole nitrogen atom. The [2-(trimethylsilyl)ethoxy]methyl moiety. Lithiation of 1-[[2-(trimethylsilyl)ethoxy]methyl]pyrrole", J. Org. Chem. 1984, 49(1), 203-205.

Murakami et al., "The Friedel-Crafts Acylation of Ethyl Pyrrole-2-carboxylate. Scope, Limitations, and Application to Synthesis of 7-Substituted Indoles", Heterocycles 1988, 27(8), 1855-1860.

Nacci et al., "Polycondensed Heterocycles. I. Synthesis of 11-Oxo-5H,11H-pyrrolo[2,1-c][1,4]benzothiazepine, Derivative of a Novel Ring System", J. Heterocycl. Chem. 1985, 22(2), 259-263.

Nacci et al., "Polycondensed Heterocycles. II. A New Preparative Route to 11-Oxo-5H,11H-pyrrolo[2,1-c][1,4]benzothiazepine", J. Heterocycl. Chem. 1986, 23(3), 769-773.

Nagarathnam et al., "Design and Synthesis of Novel α1a Adrenoceptor-Selective Dihydropyridine Antagonists for the Treatment of Benign Prostatic Hyperplasia", J. Med. Chem. 1998, 41(26), 5320-5333.

Nagel et al., "Enantioselektive Katalyse, 4. Synthese N-substituierter (R,R)-3,4-Bis(diphenylphosphino)-pyrrolidine und Anwendung ihrer Rhodiumkomplexe zur asymmetrischen Hydrierung von α-(Acylamino)acrylsäure-Derivaten", Chem. Ber. 1986, 119(11), 3326-3343.

Narasimhan et al., "A QSAR approach for the prediction of stability of benzoglycolamide ester prodrugs", Chem. Pharm. Bull. 2006, 54(8), 1067-1071.

Nelson et al., "Stereoselective Synthesis of a Potent Thrombin Inhibitor by a Novel P2-P3 Lactone Ring Opening", J. Org. Chem. 2004, 69(11), 3620-3627.

New et al., "The thieno[3,2-c]pyridine and furo[3,2-c]pyridine rings: new pharmacophores with potential antipsychotic activity", J. Med. Chem. 1989, 32(6), 1147-1156.

Newman-Evans et al., "The influence of intramolecular dynamics on branching ratios in thermal rearrangements", J. Org. Chem. 1990, 55(2), 695-711.

Nielsen et al., "Bioreversible quaternary N-acyloxymethyl derivatives of the tertiary amines bupivacaine and lidocaine—synthesis, aqueous solubility and stability in buffer, human plasma and simulated intestinal fluid", Eur. J. Pharm. Sci. 2005, 24(5), 433-440.

Nielsen et al., "Glycolamide esters as biolabile prodrugs of carboxylic acid agents: Synthesis, stability, bioconversion, and physicochemical properties", J. Pharm. Sci. 1988, 77(4), 285-298.

Nudelman et al., "Novel anticancer prodrugs of butyric acid. 2.", J. Med. Chem. 1992, 35(4), 687-694.

Nudelman et al., "The role of intracellularly released formaldehyde and butyric acid in the anticancer activity of acyloxyalkyl esters." J. Med. Chem. 2005, 48(4), 1042-1054.

Ogawa et at "Preparation of oxygen-bridged aza[15]- and aza[17]annulene dicarboxylates by intramolecular azide cyclization", Tetrahedron Lett. 1988, 29(2), 219-222.

Ojida et al., "Highly Enantioselective Reformatsky Reaction of Ketones: Chelation-Assisted Enantioface Discrimination", Org. Lett. 2002, 4(18), 3051-3054.

Ouyang et al., "Steric hindrance is a key factor in the coupling reaction of (acyloxy) alkyl-α-halides with phenols to make a new promoiety for prodrugs", Tetrahedron Lett. 2002, 43(4), 577-579.

Paine et al., "Regioselectivity of pyrrole synthesis from diethyl aminomalonate and 1,3-diketones: further observations", J. Org. Chem. 1987, 52(18), 3986-3993.

Parikh et al., "The Use of Amino Acid Oxidases for the Small-scale Preparation of the Optical Isomers of Amino Acids", J. Am. Chem. Soc. 1958, 80(4), 953-958.

Paxéus et al., "Screening for non-regulated organic compounds in municipal wastewater in Göteborg, Sweden", Water Sci. Technol. 1996, 33(6), 9-15.

Pérez-Balderas et al., "Synthesis of multivalent neoglycoconjugates by 1,3 dipolar cycloaddition of nitrile oxides and alkynes and evaluation of their lectin-binding affinities", Tetrahedron 2005, 61(39), 9338-9348.

Pfeiffer et al., "Synthesen and Eigenschaften von Pyrrolindigo-Verbindungen", Liebigs Ann. Chem. 1980(4), 564-589.

Poszavacz et al., "New Synthesis of Naratriptan", Heterocycles 2006, 68(4), 713-719.

Puterova et al., "Reaction of Substituted Furan-2-carboxaldehydes and Furo[b]pyrrole Type Aldehydes with Hippuric Acid", Molecules 2004, 9(1), 11-21.

Puterova et al., "Reactions of Substituted Furan-2-carboxaldehydes and Furo[b]pyrrole Type Aldehydes with Benzothiazolium Salts", Molecules 2004, 9(4), 241-255.

Quizon-Colquitt et al., "Porphyrins with exocyclic rings. Part 4. An improved one step synthesis of cyclopenta[b]pyrroles", J. Heterocycl. Chem. 1993, 30(2), 477-482.

Rautio et al., "Synthesis and in Vitro Evaluation of Novel Morpholinyl- and Methylpiperazinylacyloxyalkyl Prodrugs of 2-(6-Methoxy-2-naphthyl)propionic Acid (Naproxen) for Topical Drug Delivery", J. Med. Chem. 2000, 43(8), 1489-1494.

Rodriguez et al., "Conformational and molecular study of the 4-(2-carboniethyl)-1,2,3,4-tetrahydrocyclopent[b]indole", Tetrahedron 1985, 41(18), 3813-3823.

Romanova et al., "DC Polarographic and UV Spectrometric Studies of Substituted Furo[3,2-b]- and Furo[2,3-b]pyrroles", Collect. Czech. Chem. Commun. 2001, 66(11), 1615-1622.

Rosati et al., "Cephalosporins to carbapenems: 1-oxygenated carbapenems and carbapenams.", J. Med. Chem. 1990, 33(1), 291-297.

Rose et al., "Preclinical antitumor activity of water-soluble paclitaxel derivatives", Cancer Chemother. Pharmacol. 1997, 39(6), 486-492.

Salim et al., "Pharmacokinetic analysis of esteric prodrugs of valproic acid", Pharm. Res. 1990, 7(9), S222.

Sambasivarao et al., "Synthetic approach to pentaleno[2,1-b:5,4-b']diindoles", J. Org. Chem. 1990, 55(12), 3858-3866.

Sandham et al., "Synthesis and biological properties of novel glucocorticoid androstene C-17 furoate esters", Bioorg. Med. Chem. 2004, 12(19), 5213-5224.

Sandler et al., "Organic Functional Group Preparations", vol. 3; Academic Press: New York, 1972; pp. 372-381.

Satake et al., "The Reaction of Electron Excess Aromatic Heterocycle, 1,4-Dihydropyrrolo[3,2-b]pyrrole and Some Related Compounds with Chlorosulfonyl Isocyanate (CSI)", Heterocycles 1996, 43(11), 2361-2365.

Scott et al., "Preparation and Reductive Cyclization of Some Carbon-Alkylated Derivatives of Ethyl 3-Nitro-2-thienylpyruvate", J. Org. Chem. 1964, 29(8), 2165-2168.

Sergievskaya et al., "N-Bis(chloroethyl)amines with Alicyclic and Aromatic Radicals in the Molecules. II.", Zhurnal Obshchei Khimii 1958, 28, 1845-1849. [translation].

Severin et al., "Umsetzungen von Ketonen mit azavinylogen Säureamiden", Chem. Ber. 1975, 108(5), 1756-1767.

Sewald et al., "Synthesis of homochiral camphor annulated pyrrole derivatives", Tetrahedron Asymmetry 1996, 7(5), 1269-1272.

Sha et al., "Synthesis of 2,4-Dihydropyrrolo[3,4-b]pyrroles and 4,6-Dihydro-2H-dipyrrolo[3,4-b:3',4'-d]pyrroles", Heterocycles 1990, 31(4), 603-609.

Shaaya et al., "Anhydride prodrugs for nonsteroidal anti-inflammatory drugs", Pharm. Res. 2003, 20(2), 205-211.

Shek, "Chemical delivery systems and prodrugs of anticonvulsive drugs", Adv. Drug Deliv. Rev. 1994, 14(2-3), 227-241.

Shirai et al., "Reduction of 1-(m-methoxyphenyl)-4-oxocycloalkanecarbonitriles with lithium aluminum hydride", Nagoya-shiritsu Daigaku Yakugakubu Kenkyu Nenpo 1969, 17, 33-37.

Shirai et al., "Synthesis of spiro[4-hydroxycyclohexane-1,4,2',3'-dihydro-6'-methoxy-1'-substituted-2'-methyl-1'Hisoquinoline]", Chem. Pharm. Bull. 1972, 20(1), 41-46.

Shvedov et al., "Monoarylhydrazones of di- and tricarbonyl compounds in the Knorr synthesis of pyrroles", Khimiya Geterotsiklicheskikh Soedinenii 1972(3), 342-344. [translation].

Silvestri et al., "Simple, short peptide derivatives of a sulfonylindolecarboxamide (L-737,126) active in vitro against HIV-1 wild type and variants carrying non-nucleoside reverse transcriptase inhibitor resistance mutations.", J. Med. Chem. 2004, 47(15), 3892-3896.

Sivy et al., "Structure of a furo[3,2-b]pyrrole derivative", Acta Crystallogr. 1988, C44(11), 2032-2033.

Skolnick et al., "Antidepressant-like actions of DOV 21,947: a "triple" reuptake inhibitor", Eur. J. Pharmacol. 2003, 461(23), 99-104.

Slawik et al., "Lipophilicity of a series of 1,2-benzisothiazol-3(2H)-ones determined by reversed-phase thin-layer chromatography", J. Chromatogr. A 2002, 952(1-2), 295-299.

Sleath et al., "Synthesis of 7,9-didecarboxymethoxatin (4,5-dihydro-4,5-dioxo-1H-pyrrolo[2,3-f]quinoline-2-carboxylic acid) and comparison of its chemical properties with those of methoxatin and analogous o-quinones. Model studies directed toward the action of PQQ requiring bacterial oxidoreductases and mammalian plasma amine oxidase", J. Am. Chem. Soc. 1985, 107(11), 3328-3338.

Sleziak et al., "Furo[2,3-b]pyrrole Derivatives. Syntheses and Reactions in the Furan and Pyrrole Ring", Pol. J. Chem. 2000, 74(2), 207-217.

Sleziak et al., "Reactions of Furo[2,3-b]pyrrole and Furo[3,2-b]pyrrole-Type Aldehydes", Collect. Czech. Chem. Commun. 1999, 64(7), 1135-1146.

Smith et al., "Deacylation and deformylation of pyrroles", J. Org. Chem. 1983, 48(24), 4779-4781.

Snyder et al., "Synthesis of the Thieno [3,2-b]pyrrole System", J. Am. Chem. Soc. 1957, 79(10), 2556-2559.

Sohma et al., "Controlled Drug Release: Design and Application of New Water-soluble Prodrugs" in "Peptide Science 2001"; Aoyagi, H., Ed.; The Japanese Peptide Society, 2002; pp. 249-252.

Sorotskaya et al., "The Series of Substituted Butanolides and Butenolides. IV. 4-Arylidene(heteroarylidene)-2-butenolides", Zhurnal Organicheskoi Khimii 1989, 25(1), 175-182. [translation].

Soth et al., "Recherches en série hétérocyclique. XXIX. Sur des voies d'accès à des thiéno, sélénolo, furo et pyrrolopyrroles", Can. J. Chem. 1978, 56(10), 1429-1434.

Sparey et al., "The discovery of fused pyrrole carboxylic acids as novel, potent d-amino acid oxidase (DAO) inhibitors", Bioorg. Med. Chem. Lett. 2008, 18(11), 3386-3391.

STN—Registry file (RN 132857-67-1, RN 109252-80-4, RN 93144-92-4, RN 92321-04-5, RN 83957-46-4, RN 83957-32-8, RN 69740-90-5, RN 69640-94-4, RN 69640-90-0, RN 69640-89-7, RN 69640-88-6, RN 69640-87-5, RN 69640-86-4, RN 69640-85-3, RN 69640-84-2, RN 69640-83-1, RN 69640-82-0, RN 69640-80-8, RN 67313-

00-2, RN 67312-99-6, RN 67312-98-5, RN 60068-34-0, RN 60068-33-9, RN 60068-32-8, RN 58379-13-8, RN 57955-60-9, RN 57955-59-6, RN 51074-73-8, RN 51074-72-7, RN 51074-71-6, RN 51074-69-2, RN 36373-65-6, RN 36373-63-4, RN 34779-69-6, RN 34779-67-4, RN 33317-36-1, RN 33317-33-8).
STN Registry File No. 67268-37-5. Registry File. Retrieved from STN Mar. 17, 2008. One page.
Stuart et al., "Cobalt-mediated Alkylation of Siloxy Furans", Heterocycles 1991, 32(5), 949-963.
Svahn et al., "Tranexamic acid derivatives with enhanced absorption", J. Med. Chem. 1986, 29(4), 448-453.
Takahashi et al., "Asymmetric α-Substituted Phenethylamines. I. Synthesis of Optically Pure 1-Aryl-N-(2'-hydroxy-1'isopropylethyl)-2-phenylethylamines", Chem. Pharm. Bull. 1982, 30(9), 3160-3166.
Tammara et al., "Morpholinoalkyl ester prodrugs of diclofenac: synthesis, in vitro and in vivo evaluation", J. Pharm. Sci. 1994, 83(5), 644-648.
Treibs et al., "Über einige Pyrrolderivate mit angegliedertem isocyclischem Ring. Bz-Tetrahydrindole and Cyclopentenopyrrole", Justus Liebigs Ann. Chem. 1935, 517, 152-169.
Trost et al., "Palladium-Catalyzed Enantioselective C-3 Allylation of 3-Substituted-1H-Indoles Using Trialkylboranes", J. Am. Chem. Soc. 2006, 128(19), 6314-6315.
Ueda et al., "Novel water soluble phosphate prodrugs of taxol® possessing in vivo antitumor activity", Bioorg. Med. Chem. Lett. 1993, 3(8), 1761-1766.
Ueda et al., "Novel, water-soluble phosphate derivatives of 2'-ethoxy carbonylpaclitaxel as potential prodrugs of paclitaxel: Synthesis and antitumor evaluation", Bioorg. Med. Chem. Lett. 1995, 5(3), 247-252.
Urbach et al., "Eine einfache diastereoselektive Synthese von (1SR,3SR,5SR)-2-Azabicyclo [3.3.0] octan-3-carbonsäure", Tetrahedron Lett. 1985, 26(15), 1839-1842.
van Herk et al., "Pyrazole Derivatives as Partial Agonists for the Nicotinic Acid Receptor", J. Med. Chem. 2003, 46(18), 3945-3951.
Vicini et al., "Biological studies on 1,2-benzisothiazole derivatives. I. Evaluation of antibacterial, antifungal and DNA-damaging activity", Farmaco 1989, 44(5), 511-517.
Vicini et al., "Sintesi e proprieta antiflogistiche antipiretiche ed analgesiche di 5-(1,2-benzisotiazolil)tetrazoli", Farmaco Sci. 1986, 41(2), 111-118.
Vicini et al., "Sintesi e proprieta antiflogistiche antipiretiche ed analgesiche di acidi 5-benzisotiazolilalcanoici e di loro derivati funzionali", Farmaco Sci. 1984, 39(10), 817-829.
Vippagunta et al., "Crystalline solids", Adv. Drug Deliv. Rev. 2001, 48(1), 3-26.
Viswanathan et al., "Free Radical-Mediated Aryl Amination and its use in a Convergent [3+2] Strategy for Enantioselective Indoline α-Amino Acid Synthesis", J. Am. Chem. Soc. 2003, 125(1), 163-168.
Vitali et al., "Ricerche nella classe dei fitocidi 3-benzisotiazolacetici", Farmaco Sci. 1973, 28(1), 8-18.
Vogel et al., "Cycloalkano-2H-pyrrole als stabile Zwischenstufen bei der Umwandlung von β-Cycloalkenyl-α-azidoacrylestern in Cycloalkano-1H-pyrrole", Angew. Chem. 1993, 105(7), 1116-1117.
Vogel et al., "Cycloalkano-2H-pyrrole as a Stable Intermediate in the Conversion of beta-Cycloalkenyl-alpha-azidoacrylates to Cycloalkano-1H pyrroles", Angew. Chem. Int. Ed. Engl. 1993, 32(7), 1051-1052. [translation of Angew. Chem. 1993, 105(7), 1116-1117.].
Wang et al., "Synthesis of ethyl cyclopenteno- or cyclohexeno[b]pyrrolyl-2-carboxylates", Youji Huaxue 1997, 17(6), 524-528.
Watanabe et al., "Enantioselective addition of chirally modified allylboranes to N-(trimethylsilyl)benzaldehyde imine", Tetrahedron Asymmetry 1995, 6(7), 1531-1534.
Welch et al., "Improved Syntheses of [3,2-b]- and [2,3-b]-fused Selenolo- and Thienopyrroles, and of Furo[3,2-b]pyrrole", Heterocycl. Comm. 1999, 5(4), 305-310.
Wen et al., "Cell differentiation enhancement by hydrophilic derivatives of 4,8-Dihydrobenzo[1,2-b:5,4-b']dithiophene-4,8-diones in HL-60 leukemia cells", Bioorg. Med. Chem. Lett. 2007, 17(10), 2908-2912.
Wensbo et al., "Indole-3-Acetic Acids and Hetero Analogues by One Pot Synthesis including Heck Cyclisation", Tetrahedron 1995, 51(37), 10323-10342.

Wensbo et al., "Indole-3-pyruvic acid oxime ethers and thieno analogues by Heck cyclisation. Application to the synthesis of thia-tryptophans", Tetrahedron 1996, 52(47), 14975-14988.
Wernly-Chung et al., "Structure-reactivity relationships in the chemical hydrolysis of prodrug esters of nicotinic acid", Int. J. Pharm. 1990, 63(2), 129-134.
West, A. R., "Solid State Chemistry and its Applications"; Wiley: New York, 1988; pp. 358 and 365.
Wright et al., "Derivatives of 11-(1-piperazinyl)-5H-pyrrolo[2,1-c][1,4]benzodiazepine as central nervous system agents", J. Med. Chem. 1980, 23(4), 462-465.
Xue et al., "An Efficient Synthesis of Glycoprotein IIb/IIIa Inhibitor DMP728. A Novel Synthesis of N.alpha.-Methylarginine-Containing Peptide", J. Org. Chem. 1995, 60(4), 946-952.
Yardley et al., "2-Phenyl-2-(1-hydroxycycloalkyl)ethylamine derivatives: synthesis and antidepressant activity", J. Med. Chem. 1990, 33(10), 2899-2905.
Yarovenko et al., "Regioselective acylation of methyl 2-methyl-4H-thieno[3,2-b]pyrrole-5-carboxylate", Russ. Chem. Bull., Int. Ed., 2003, 52(2), 451-456.
Yasuhara et al., "Prodrugs of 3-(3,4-dichlorobenzyloxy)-2-amino-6-fluorobicyclo[3.1.0]hexane-2,6-dicarboxylic acid (MGS0039): A potent and orally active group II mGluR antagonist with antidepressant-like potential", Bioorg. Med. Chem. 2006, 14(12), 4193-4207.
Yevich et al., "Synthesis and biological evaluation of 1-(1,2-benzisothiazol-3-yl)- and (1,2-benzisoxazol-3-yl)piperazine derivatives as potential antipsychotic agents", J. Med. Chem. 1986, 29(3), 359-369.
Yu et al., "The regiospecific C-4 lithiation of 2-(tert-butyldimethylsilyl)-3-furoic acid", J. Chem. Soc., Perkin Trans. 1, 1991(10), 2600-2601.
Yudina et al., "Synthesis and alkylation of indolo[3,2-b]carbazoles", Tetrahedron 2003, 59(8), 1265-1275.
Zani et al., "Biological studies on 1,2-benzisothiazole derivatives. VI. Antimicrobial activity of 1,2-benzisothiazole and 1,2-benzisothiazolin-3-one derivatives and of some corresponding 1,2-benzisoxazoles", Farmaco 1996, 51(11), 707-713.
Zaragoza Dörwald, F., "Side Reactions in Organic Synthesis"; Wiley-VCH: Weinheim, 2005; pp. IX and 41.
Zhang et al., "Synthesize the china 3-pyridyl ester analogs of anaddicted analgesic Epibatidine", Journal of Shangqiu Teachers College (Shangqiu Shifan Xueyuan Xuebao) 2004, 20(5), 90-94.
Zhang et al., "Total synthesis of the porphyrin mineral abelsonite and related petroporphyrins with five-membered exocyclic rings", Tetrahedron Lett. 2003, 44(39), 7253-7256.
Zinoune et al., "Aminoalkylation of Aldehydes with Glyoxal N,N-Dimethlmonohydrazone Yields Stable 4-Substituted Pyrrolin-3-ones", Heterocycles 1989, 28(2), 1077-1084.
Zong et al., "A new and efficient synthetic route toward 3,4-alkylenedioxypyrrole (XDOP) derivatives via Mitsunobu chemistry", Tetrahedron Lett. 2006, 47(21), 3521-3523.
Andersen, Peter H., "Biochemical and Pharmacological Characterization of [$^3$H]GBR 12935 Binding In Vitro to Rat Striatal Membranes: Labeling of the Dopamine Uptake Complex", J. Neurochemistry, 48, 1887-1896, (1987).
Childers et al., "Lecozotan Hydrochloride: Cognition Enhancer, Treatment of Alzheimer's Disease, Competitive 5-HT1A Receptor Antagonist", Drugs of the Future, 32(5). 339-407 (2007).
Clague et al., "Action of Agonists and Antagonists at Muscarinic Receptors Present on Ileum and Atria In Vitro", British J. Pharmacology, 86, 163-170 (1985).
Deninno et al., The Preparation and Intra- and Intermolecular Addition Reactions of Acyclic N-Acylimines: Application to the Synthesis of (±)-Sertraline, J. Organic Chemistry, 66, 6988-6993 (2001).
Dews, Peter B., "The Measurement of the Influence of Drugs on Voluntary Activity in Mice", British J. Pharmacology, 8, 46-48 (1953).
Emsley, Robin, "Drugs in Development for the Treatment of Schizophrenia," Expert Opin. Investig. Drugs, 18(8), 1103-1118 (2009).
Fuller et al., "Comparison of Desmethylsertraline With Sertraline as a Monoamine Uptake Inhibitor In Vivo", Prog. Neuro-Psychopharmacol. & Biol. Psychiatry, 19, 135-149 (1995).

Galli et al., "Sodium-Dependent Norepinephrine-Induced Currents in Noreprinephrine-Transporter-Transfected HEK-293 Cells Blocked by Cocaine and Antidepressants", *J. Exper. Biology*, 198, 2197-2212 (1995).

Giros et al., "Cloning, Pharmacological Characterization, and Chromosome Assignment of the Human Dopamine Transporter", *Molecular Pharmacology*, 42, 383-390 (1992).

Gonzalez-Viejo et al., "A Comparative Study of Fibromyalgia Treatment: Ultrasonography and Physiotherapy Versus Sertraline Treatment", *Annales de réadaption et de médecine physique*, 48, 610-615 (2005).

Goodnick et al., "Sertraline in Diabetic Neuropathy: Preliminary Results", *Annals of Clin. Psychiatry*, 9(4), 255-257 (1997).

Goodnick, Paul J., "Use of Antidepressants in Treatment of Comorbid Diabetes Mellitus and Depression as Well as in Diabetic Neuropathy", *Annals of Clin. Psychiatry*, 13(1), 31-41 (2001).

Gu et al., "Stable Expression of Biogenic Amine Transporters Reveals Differences in Inhibitor Sensitivity, Kinetics, and Ion Dependence", *J. Biol. Chem.*, 269(10), 7124-7130 (1994).

Hamelin et al., "The Disposition of Fluoxetine but not Sertraline is Altered in Poor Metabolizers of Debrisoquin", *Clinical Pharmacology & Therapeutics*, 60(5), 512-521 (1996).

Harrison et al., "Compendium of Organic Synthetic Methods", 258-259 (1971).

Janowsky et al., "Characterization of Sodium-Dependent [$^3$H]GBR-12935 Binding in Brain: A Radioligand for Selective Labelling of the Dopamine Transport Complex", *J. Neurochemistry*, 46, 1272-1276 (1986).

Kim & Chung, "An Experimental Model for Peripheral Neuropathy Produced by Segmental Spinal Nerve Litigation in the Rat", 50, 355-363 (1992).

Koe et al., "Sertraline, 1S;4S-N-Methyl-4-(3,4-Dichlorophenyl)-1,2,3,4-Tetrahydro-1-Naphthylamine, a New Uptake Inhibitor with Selectivity for Serotonin", *J. Pharmacology & Experimental Therapeutics*, 226(3). 686-700 (1983).

Lifsehytz et al., "Sex-dependent Effects of Fluoxetine and Triiodothyronine in the Forced Swim Test in Rats", *Euro. Nueropsychopharmacology*, 16, 115-121 (2006).

Maehr, Hubert, "A Proposed New Convention for Graphic Presentation of Molecular Geometry and Topography", *J. Chem. Educ.*, 62, 114-120 (1985).

Mckelvy, J. F., "AV965, A Selective 5-HT1A Silent Antagonist as a Candidate for Adjunctive Treatment of Cognitive Impairment in Schizophrenia," *International Congress of Schizophrenia Research, Schizophrenia Bulletin*, 31(2), 305 (2005).

Pacholczyk et al., "Expression Cloning of a Cocaine- and Antidepressant-Sensitive Human Noradrenalin Transporter", *Letters to Nature*, 350, 350-354 (1991).

Perovic & Muller, "Pharmacological Profile of Hypericum Extract", *Arzneim-Forseh/Drug Res.*, 45(11), 1145-1148 (1995).

Porsolt et al., "Behavioural Despair in Mice: a Primary Screening Test for Antidepressants", *Arch Int. Pharmacdoyn*, 229, 327 336 (1977).

Pristupa et al., "Pharmacological Heterogeneity of the Cloned and Native Human Dopamine Transporter: Disassociation or [$^3$H]WIN 35,428 and [$^3$H]GBR 12,935 Binding", *ASPET*, 45, 125-135 (1994).

Ronfeld et al.. "Pharmacokinetics of Sertraline and its N-Demethyl Metabolite in Elderly and Young Male and Female Volunteers", *Clinical Pharmacokinet.*, 32, 22-30 (1997).

Sanchez & Hyttel, "Comparison of the Effects of Antidepressants and Their Metabolites on Reuptake of Biogenic Amines and on Receptor Binding", *Cellular and Molecular Neurobiology*, 19(4), 467-489 (1999).

Semenchuk et al., "Double-Blind, Randomized Trial of Bupropion SR for the Treatment of Neuropathic Pain", *Neurology*, 57, 1583-1588 (2001).

Serebruany et al., "Platelet Inhibition by Sertraline and N-Desmethylsertraline: A Possible Missing Link Between Depression, Coronary Events, and Mortality Benefits of Selective Serotonin Reuptake Inhibitors", *Pharmacological Research*, 43(5), 453-461 (2001).

Tang et al., "An Ortho-Substituted B1PHEP Ligand and its Applications in Rh-Catalyzed Hydrogenation of Cyclic Enamides", *Organic Letters*, 4(10), 1695-1698 (2002).

Tatsumi et at, "Pharmacological Profile of Antidepressants and Related Compounds at Human Monoamine Transporters", *Euro. J. Pharrna.*, 340. 249-258 (1997).

Vazquez-Palacios et al., "Antidepressant-Like Effects of the Acute and Chronic Administration of Nicotine in the Rat Forced Swimming Test and its Interaction with Flouxetine", *Pharmacology, Biochemistry and Behavior*, 78, 165-169 (2004).

Welch et at, "Nontricyclic Antidepressant Agents Derived from cis- and trans-1-Amino-4-aryltetralins" *J. Med. Chem.*, 27, 1508-1515 (1984).

Wheeler-Aceto et al., "Standardization of the Rat Paw Formalin Test for the Evaluation of Analgesics", *Psychopharmacology*, 104, 35-44 (1991).

Witchel et al., "Inhibitory Actions of the Selective Serotonin Reuptake Inhibitor Citalopram on HERG and Ventricular L-type Calcium Currents", *FEBS Letters*, 512, 59-66 (2002).

Wong et al., "Norfluoxetine Enantiomers as Inhibitors of Serotonin Uptake in Rat Brain", *Neuropsychopharmacology*, 8(4), 337-344 (1993).

Yaksh et al., "An Automated Flinch Detecting System for Use in the Formalin Nociceptive Bioassay", *J. Appl. Physiol.*, 90, 2386-2402 (2001).

Communication pursuant to Article 96(2) EPC, dated Nov. 30, 2007 from the European Patent Office for European Application No. 03754641.3-2103, cover page and pp. 1-5.

Notice of Allowance for U.S. Appl. No. 11/416,586 dated Apr. 29, 2008.

ISR & WO for International Patent Application No. PCT/US07/65585 dated Oct. 3, 2008.

ISR & WO for International Patent Application No. PCT/US03/29110 dated Mar. 2, 2004.

* cited by examiner

PREPARATION OF CHIRAL AMIDES AND AMINES

CROSS REFERENCE TO RELATED APPLICATIONS

This application is a U.S. National Phase Application of PCT/US2007/065659 filed Mar. 30, 2007 and claims priority under 35 U.S.C. §119(e) to U.S. Provisional Patent Application No. 60/787,837 filed Mar. 31, 2006, which applications are incorporated herein by reference in their entirety for all purposes.

FIELD OF THE INVENTION

This invention relates to processes suitable for the large-scale preparation of enantiomerically- or diastereomerically-enriched chiral amides and amines prepared by these processes.

BACKGROUND OF THE INVENTION

Enantiomerically-enriched chiral primary amines are commonly used as resolving agents for racemic acids, as chiral auxiliaries for asymmetric syntheses and as ligands for transition metal catalysts used in asymmetric catalysis. In addition, many pharmaceuticals, such as sertraline, contain chiral amine moieties. Effective methods for the preparation of such compounds are of great interest to the pharmaceutical industry. Particularly valuable are processes that allow for the preparation of each enantiomer or diastereomer, in enantiomeric or diastereomeric excess, as appropriate, from prochiral or chiral starting materials.

Methods are available for the preparation of enantiomerically enriched amines. For example, the addition of organometallic reagents to imines or their derivatives is reported by Watanabe et al., *Tetrahedron Asymm.* (1995)6:1531; Denmark et al., *J. Am. Chem. Soc.* (1987) 109:2224; Takahashi et al., *Chem. Pharm. Bull.* (1982) 30:3160; and the addition of organometallic reagents to chiral oxazolidines is disclosed by Mokhallalatiet et al., *Tetrahedron Lett.* (1994) 35:4267. Although some of these methods are widely employed, few are amenable to large-scale production of amines.

Other approaches involve optical resolution of a single enantiomer or diastereomer from a mixture. Resolution may be conducted through stereoselective biotransformations or by the formation of diastereomeric salts that are separated by crystallization. The utility and applicability of resolution methods relying on selective recrystallization are often limited by the lack of availability of appropriate chiral auxiliaries. In addition, resolution processes upon racemic mixtures afford a maximum yield of 50% for either stereoisomer. Therefore, the resolution of racemic mixtures is generally viewed as an inefficient process.

The preparation of an enantiomerically-enriched amine via conversion of a precursor oxime to the corresponding enamide, which is subsequently converted to the amine through asymmetric hydrogenation and deprotection, has been described (WO 99/18065 to Johnson et al.). The processes are, however, not of general applicability to a wide range of substrates. Moreover, many of the recognized processes require a large excess of metallic reagent to effect the conversion. The result is the generation of significant amounts of solid metal waste, a trait that is undesirable for large-scale production processes.

Therefore, a cost-efficient, scalable method for the conversion of oximes to corresponding enamides, which does not rely on a metallic reagent, is needed. The facile, high yield conversion of readily accessible oximes to the corresponding enamides without the use of metallic reagents would be a valuable step towards the large-scale synthesis of chiral amides and amines. The current invention addresses this and other needs.

SUMMARY OF THE INVENTION

The present invention provides an efficient and convenient method for the conversion of an oxime to the corresponding enamide. The method of the invention accomplishes the desired conversion without the use of a metallic reagent. The method is appropriate for large-scale synthesis of enamides, amides, amines, and their derivatives.

Thus, in a first aspect, the current invention provides a method for converting an oxime into an enamide. The method includes contacting the oxime with a phosphine and an acyl donor, under conditions appropriate to convert the oxime into the enamide. The method produces enamides in high yields and is generally applicable across a wide range of oxime structures. The enamides are readily converted to the corresponding amines. In an exemplary route, described in greater detail herein, the enamide is reduced to the corresponding amide, which is subsequently deacetylated to provide the amine.

The method is particularly useful for the large-scale synthesis of bioactive species, such as those having the 1,2,3,4-tetrahydro-N-alkyl-1-naphthalenamine or 1,2,3,4-tetrahydro-1-naphthalenamine substructure. Examples of bioactive compounds with this substructure include sertraline and sertraline analogs, and the trans isomers of sertraline, norsertraline and analogs thereof. Sertraline, (1S,4S)-cis 4-(3,4-dichlorophenyl)-1,2,3,4-tetrahydro-N-methyl-1-naphthalenamine, is approved for the treatment of depression by the United States Food and Drug Administration, and is available under the trade name ZOLOFT® (Pfizer Inc., NY, N.Y., USA). In human subjects, sertraline has been shown to be metabolized to (1S,4S)-cis 4-(3,4-dichlorophenyl)-1,2,3,4-tetrahydro-1-naphthalenamine, also known as desmethylsertraline or norsertraline.

Enamides provide a convenient precursor to compounds that include the 1,2,3,4-tetrahydro-N-alkyl-1-naphthalenamine or 1,2,3,4-tetrahydro-1-naphthalenamine substructure. Accordingly, in a second aspect, the present invention provides a method of converting an oxime having the formula:

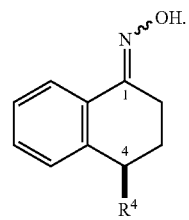

into an enamide having the formula:

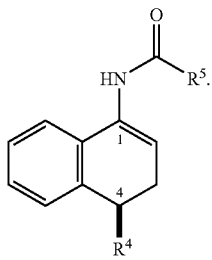

In the formulae above, the symbol $R^4$ represents substituted or unsubstituted aryl or substituted or unsubstituted heteroaryl. The symbol $R^5$ represents H, substituted or unsubstituted alkyl, substituted or unsubstituted heteroalkyl, substituted or unsubstituted aryl, substituted or unsubstituted heteroaryl or substituted or unsubstituted heterocycloalkyl. The method includes contacting said oxime with a phosphine and an acyl donor under conditions appropriate to convert said oxime to said enamide.

In a third aspect, the invention provides a mixture comprising:

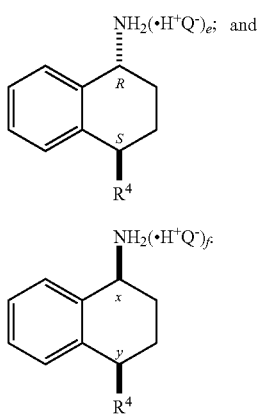

In the formulae above, $Q^-$ is an anion. The indices e and f are independently selected numbers from 0 to 1. The indices x and y independently represent (R) or (S). In an exemplary embodiment, when x is (R), y is (R) and when x is (S), y is (S). In another exemplary embodiment, when x is (S), y is (R).

The present invention provides a general and efficient method for converting oximes to enamides. Moreover, the invention provides a method for the stereoselective synthesis of sertraline and sertraline analogs, and the trans isomers of sertraline, norsertraline and analogs thereof. Additional objects, advantages and embodiments of the present invention are set forth in the detailed description that follows.

DETAILED DESCRIPTION OF THE INVENTION

Abbreviations

As used herein, "COD" means 1,5-cyclooctadiene.

DEFINITIONS

Where substituent groups are specified by their conventional chemical formulae, written from left to right, they equally encompass the chemically identical substituents, which would result from writing the structure from right to left, e.g., —CH$_2$O— is preferably intended to also recite —OCH$_2$—.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also preferably include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species. Alkyl groups are preferably substituted, e.g., with one or more groups referred to hereinbelow as an "alkyl group substituent."

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Two or more heteroatoms may be consecutive, such as, for example, —CH$_2$—NH—OCH$_3$ and —CH$_2$—O—Si(CH$_3$)$_3$—. Similarly, the term "heteroalkylene" by itself or as part of another substituent refers to a substituted or unsubstituted divalent heteroalkyl radical, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents —C(O)$_2$R'— and, preferably, —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) preferably includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

When the compound prepared by a method of the invention is a pharmacological agent, the salt is preferably a pharmaceutically acceptable salt. Examples of pharmaceutically acceptable salts are presented hereinabove, and are generally known in the art. See, for example, Wermuth, C., PHARMACEUTICAL SALTS: PROPERTIES, SELECTION AND USE—A HANDBOOK, Verlag Helvetica Chimica Acta (2002)

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogs. Other examples of prodrugs include compounds that comprise NO, $NO_2$, —ONO, or —$ONO_2$ moieties. The term "prodrug" is accorded a meaning herein such that prodrugs do not encompass the parent compound of the prodrug. When used to describe a compound of the invention, the term "prodrug" may also interpreted to exclude other compounds of the invention.

As used herein, and unless otherwise indicated, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "biohydrolyzable ester" means an ester of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters.

As used herein, and unless otherwise indicated, the term "biohydrolyzable amide" means an amide of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable amides include, but are not limited to, lower alkyl amides, α-amino acid amides, alkoxyacyl amides, and alkylaminoalkylcarbonyl amides.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

As used herein, and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein, the term "substantially free of its cis stereoisomer" means that a mixture of a compound is made up of a significantly greater proportion of its trans stereoisomer than of its optical antipode. In a preferred embodiment of the invention, the term "substantially free of its cis stereoisomer" means that the compound is made up of at least about 90% by weight of its trans stereoisomer and about 10% by weight or less of its cis stereoisomer. In a more preferred embodiment of the invention, the term "substantially free of its cis stereoisomer" means that the compound is made up of at least about 95% by weight of its trans stereoisomer and about 5% by weight or less of its cis stereoisomer. In an even more preferred embodiment, the term "substantially free of its cis stereoisomer" means that the compound is made up of at least about 99% by weight of its trans stereoisomer and about 1% or less of its cis stereoisomer.

The graphic representations of racemic, ambiscalemic and scalemic or enantiomerically pure compounds used herein are taken from Maehr, *J. Chem. Ed.*, 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and "diastereomeric excess" are used interchangeably herein. Compounds with a single stereocenter are referred to as being present in "enantiomeric excess." Those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, e.g., tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The present invention provides a non-metal mediated method for the conversion of oximes to the corresponding enamides. The enamides are formed in high yields and purities, making them suitable substrates for homogeneous asymmetric hydrogenation, a process that affords enantiomerically-enriched amides. The amides can be deprotected to furnish enantiomerically-enriched amines. Either enantiomer of the amine may be obtained by this method. Ketones and aldehydes can thus be transformed into enantiomerically-enriched chiral amines. The process is amenable to large-scale production.

Methods

A. Oxime to Enamide

In a first aspect, the present invention provides a method for converting an oxime into an enamide. The method includes contacting the oxime with a phosphine and an acyl donor, under conditions appropriate to convert the oxime into the enamide. Exemplary conditions are set forth herein.

In one embodiment, the oxime of use in the method of the invention has the formula:

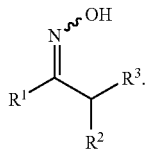

The symbols $R^1$, $R^2$ and $R^3$ represent radicals that are independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. At least two of $R^1$, $R^2$ and $R^3$ are optionally joined to form a ring system selected from substituted or unsubstituted cycloalkyl, substituted or unsubstituted heterocycloalkyl, substituted or unsubstituted aryl and substituted or unsubstituted heteroaryl.

In another exemplary embodiment, the oxime has the formula:

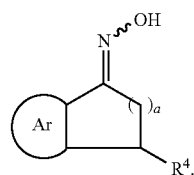

The symbol Ar represents substituted or unsubstituted aryl or substituted or unsubstituted heteroaryl. $R^4$ is H, substituted or unsubstituted alkyl, substituted or unsubstituted heteroalkyl, substituted or unsubstituted aryl, substituted or unsubstituted heteroaryl or substituted or unsubstituted heterocycloalkyl. The index a is an integer from 1 to 4.

In an exemplary embodiment according to this aspect, $R^4$ is substituted or unsubstituted aryl (e.g., phenyl). In a further exemplary embodiment, $R^4$ is phenyl substituted with at least one halogen atom.

In yet another exemplary embodiment, $R^4$ has the formula:

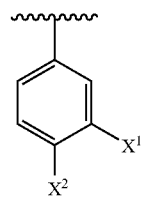

in which the symbols $X^1$ and $X^2$ represent independently selected halo moieties. In a preferred embodiment, $X^1$ and $X^2$ are each chloro.

In another exemplary embodiment, the oxime has the formula:

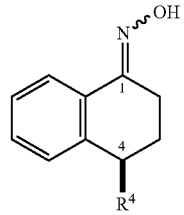

wherein $R^4$ is selected from substituted or unsubstituted aryl and substituted or unsubstituted heteroaryl.

In a further exemplary embodiment, the oxime has the formula:

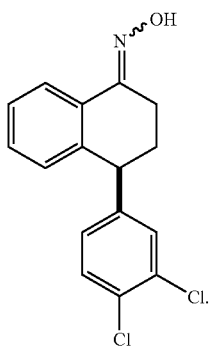

The preparation of oximes is well known in the art and a wide range of methods is known and readily practiced by those of skill in the art. Typically, oximes are prepared by reaction of ketones or aldehydes with hydroxylamine (or alkyloxyamine) under one of a variety of conditions. See, e.g., Sandler and Karo, "ORGANIC FUNCTIONAL GROUP PREPARATIONS," Vol. 3, pp 372-381, Academic Press, New York, 1972.

In an exemplary embodiment, optically pure tetralone is converted into the corresponding oxime according to Scheme 1.

Scheme 1

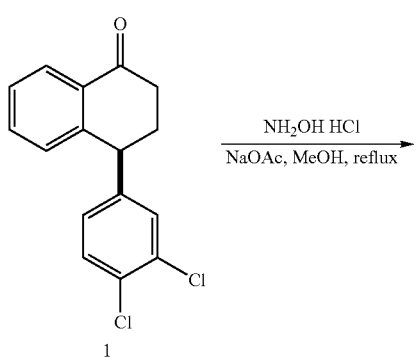

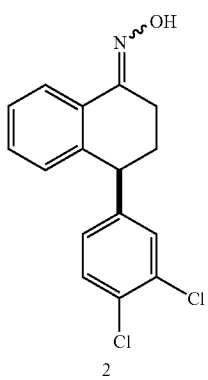

In Scheme 1, optically pure tetralone 1 is treated with hydroxylamine hydrochloride, and sodium acetate in methanol to afford the oxime 2. Compound 2 can either be isolated or carried forward as a solution in a suitable solvent to the next step. In another method, a ketone is converted to the corresponding oxime in an aromatic hydrocarbon solvent, e.g., toluene.

According to the process of the invention, the oxime is converted into an enamide. In an exemplary embodiment, the enamide has the formula:

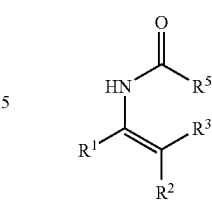

in which $R^1$-$R^3$ are as discussed above and $R^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

In another exemplary embodiment, the enamide has the formula:

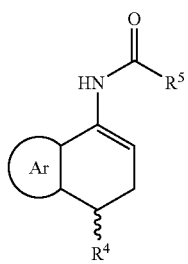

in which $R^4$ is selected from substituted or unsubstituted aryl and substituted or unsubstituted heteroaryl. $R^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

An exemplary enamide has the formula:

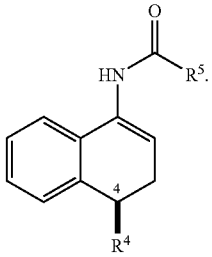

In an exemplary embodiment according to this aspect, C-4 of the ketone, oxime and enamide is of (S)-configuration.

In a preferred embodiment, the enamide has the formula:

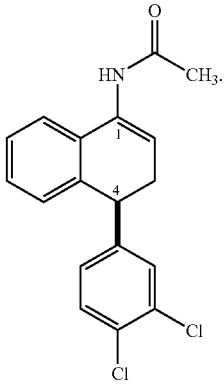

C-4 has a configuration selected from (R) and (S) and, in a preferred embodiment, C-4 is of (S)-configuration. In another embodiment, the method provides an enamide mixture including both (S)- and (R)-enantiomers.

Acyl Donor

Acyl donors of essentially any structure are of use in the present invention. An exemplary acyl donor has the formula:

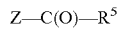

in which Z is a leaving group. $R^5$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

In an exemplary embodiment, the acyl donor is an acid anhydride, in which Z has the formula:

in which $R^6$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

In another exemplary embodiment, $R^5$ and $R^6$ are independently selected substituted or unsubstituted $C_1$-$C_4$ moieties.

In another embodiment, the acyl donor is an anhydride, preferably acetic anhydride ($Ac_2O$).

In another exemplary embodiment, the acyl donor is a member selected from an acid chloride (Z=Cl) and an activated ester, e.g., an N-hydroxy succinimidyl ester.

The acyl donor can be present in any useful amount and selection of this amount is within the abilities of those of skill in the art. In an exemplary embodiment, the acyl donor is used in an amount from about 1 to about 3 equivalents, preferably from about 1 to about 2 equivalents and, more preferably, from about 1 to about 1.5 equivalents relative to the oxime substrate.

Phosphine

Phosphorus reagents, such as phosphines, of any structure are of use in practicing the present invention. For example, in general, phosphines have the formula:

in which each Q is independently selected from H, substituted or unsubstituted alkyl and substituted or unsubstituted aryl.

In an exemplary embodiment, each Q is a member independently selected from substituted or unsubstituted $C_1$-$C_6$ alkyl and substituted or unsubstituted phenyl. Presently preferred phosphorus reagents include, but are not limited to, diphenylphosphine ($Ph_2PH$), triphenylphosphine ($Ph_3P$), tri-n-butylphosphine (n-$Bu_3P$), triethylphosphine ($Et_3P$), tri-n-propylphosphine (n-$Pr_3P$), 1,2-bisdiphenylphosphinoethane ($Ph_2PCH_2CH_2PPh_2$), diethyl phosphite ($Et_2OP(O)H$), triphenyl phosphite (($PhO)_3P$), P-chlorodiphenylphosphine ($Ph_2PCl$), methyltriphenylphosphonium bromide ($MePh_3PBr$), and benzyltriphenylphosphonium chloride ($BnPh_3PCl$).

The phosphorus reagent, such as phosphine, is incorporated into the reaction mixture in substantially any useful amount. Exemplary reactions of the invention utilize from about 0.5 equivalents to about 5 equivalents, preferably from about 1 equivalent to about 3 equivalents and, more preferably, from about 1.1 equivalents to about 2 equivalents of the phosphorus reagent with respect to the carbonyl-containing substrate.

Solvent

In an exemplary embodiment, the oxime is contacted with the phosphorus reagents (e.g., phosphine) and the acyl donor in the presence of an organic solvent. The solvent can be a protic or an aprotic solvent. In a preferred embodiment, the solvent is an aprotic solvent. In a further preferred embodiment, the aprotic solvent is an aromatic solvent (e.g., toluene, xylene and combinations thereof).

In an exemplary embodiment, in which the oxime is compound 3, the solvent is preferably toluene.

B. Enamide to Amide

In another aspect, the current invention provides a method for converting an enamide to an amide. The method includes, contacting the enamide with a hydrogenation catalyst and hydrogen or a hydrogen transfer reagent under conditions appropriate to hydrogenate a carbon-carbon double bond of the enamide, thereby converting the enamide to an amide.

The methods of the present invention are not limited to practice on enamides characterized by any particular structural element or membership within any single structural class. The methods disclosed herein are of broad applicability across a wide range of enamide structures. Exemplary reagents and reaction conditions for the conversion of the enamide to the amide are set forth below.

Catalyst

The carbon-carbon double bonds of the enamides are reduced by processes such as hydrogen transfer, in which a hydrogen-donor such as a secondary alcohol, and in particular isopropanol is used; and hydrogenation, in which molecular hydrogen is used. Both hydrogen transfer and hydrogenation processes require a catalyst or catalytic system to activate the reducing agent, namely an alcohol or molecular hydrogen, respectively.

In selected embodiments of the present invention, the enamide substrate is chiral or prochiral and the reduction, hydrogen transfer or hydrogenation is performed in a stereoselective manner. In this embodiment, it is generally preferred that the catalyst is a chiral catalyst. Also preferred is that the chiral catalyst is a transition metal catalyst.

Numerous reports have been published on chiral transition metal complex catalysts usable in catalytic asymmetric hydrogenation reactions. Among these, transition metal complexes of ruthenium, iridium, rhodium, palladium, nickel or the like, which contain optically active phosphines as ligands, have been reported to exhibit excellent performance as catalysts for asymmetric synthetic reactions, and some of them are already used in industrial application. See, e.g., ASYMMETRIC CATALYSIS IN ORGANIC SYNTHESIS, Ed., R. Noyori, Wiley & Sons (1994); and G. Franciò, et al., *Angewandte Chemie. Int. Ed.*, 39: 1428-1430 (2000).

In a preferred embodiment, the metal in the catalyst is rhodium (Rh), ruthenium (Ru) or iridium (Ir).

In an exemplary embodiment, the hydrogenation catalyst used in the present methods is a chiral complex of a transition metal with a chiral phosphine ligand, including monodentate and bidentate ligands. For example, preferred bidentate ligands include 1,2-bis(2,5-dimethylphospholano)ethane (MeBPE), P,P-1,2-phenylenebis {(2,5-endo-dimethyl)-7-phosphabicyclo[2.2.1]heptane} (MePennPhos), 5,6-bis (diphenylphosphino) bicyclo[2.2.1]hept-2-ene (N or Phos) and 3,4-bis(diphenylphosphino) N-benzyl pyrrolidine (commercially available as catASium® D).

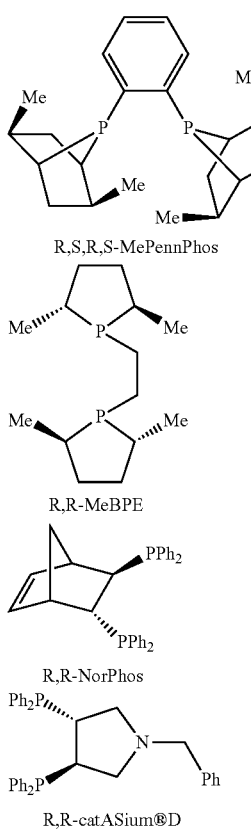

R,S,R,S-MePennPhos

R,R-MeBPE

R,R-NorPhos

R,R-catASium®D

In a preferred embodiment for making the amide derived from tetralones, the chiral catalyst is (R,S,R,S)-MePennPhos (COD)RhBF$_4$, (R,R)-MeBPE(COD)RhBF$_4$, (R,R)—N or Phos(COD)RhBF$_4$ (Brunner et al., *Angewandte Chemie* 91(8): 655-6 (1979)), or (R,R)-catASium® D(COD)RhBF$_4$ (Nagel et al., *Chemische Berichte* 119(11): 3326-43 (1986)).

The catalyst is present in the reaction mixture in any useful amount. Determining an appropriate catalyst structure and an effective amount of this catalyst is well within the abilities of those skilled in the art. In an exemplary embodiment, the catalyst is present in an amount of from about 0.005 mol % to about 1 mol % Generally, it is preferred that the catalyst be present in an amount of from about 0.01 mol % to about 0.5 mol % and, even more preferably, from about 0.02 mol % to about 0.2 mol %.

In an exemplary embodiment, the enamide is hydrogenated to the corresponding amide in the presence of from about 0.02 to about 0.3 mol %, preferably, from about 0.03 to about 0.2 mol %, and even more preferably, from about 0.03 to about 0.1 mol % Rh-MeBPE catalyst.

In another exemplary embodiment, the enamide is hydrogenated to give the amide in the presence of about 0.1 to about 1.0 mol %, preferably about 0.1 to about 0.5 mol % and, more preferably about 0.3 mol % of a Rh-PennPhos catalyst.

In another exemplary embodiment, the enamide is hydrogenated to give the amide in the presence of about 0.005 to about 1.0 mol %, preferably about 0.01 to about 0.5 mol % and, more preferably about 0.02 to about 0.1 mol % of (R,R)—NorPhos(COD)RhBF$_4$ catalyst.

A presently preferred catalyst of use in the invention provides the amide in a high yield of at least 85%, preferably at least 90% and more preferably at least 95% yield from the enamide. A generally preferred catalyst is one that provides high yields of amides when the synthesis is on a large scale of at least 300 grams, preferably at least 500 grams, more preferably at least 750 grams and even still more preferably at least 1,000 g. Preferred catalysts provide the amides in the high yield set forth above when the reaction is carried out on the large scale, also set forth above. An exemplary catalyst having these desirable properties is (R,R)—N or Phos(COD)RhBF$_4$.

Hydrogen Pressure

When the conversion of the C—C double bond of the enamide to the corresponding C—C single bond is effected by hydrogenation, the pressure of the hydrogen in the reaction vessel can be adjusted to optimize the reaction yield and stereoselectivity. The methods of the invention are practiced with any useful hydrogen pressure, and those with skill in the art will understand how to adjust the hydrogen pressure to optimize the desired result.

In an exemplary embodiment, the enamide is hydrogenated, to afford the amide, at a hydrogen pressure of about 2 to about 10 bar, preferably about 4 to about 8 bar and, more preferably, about 5 to about 6 bar.

Solvent

The methods of the invention are not limited to practice with any one solvent or any class of solvents, e.g. protic, aprotic, aromatic, or aliphatic. Choice of an appropriate solvent for a particular reaction is well within the abilities of those of skill in the art.

In an exemplary embodiment, the enamide is converted to the amide in the presence of a solvent, which is a protic solvent, an aprotic solvent, or a mixture thereof. In a preferred embodiment the solvent is a protic solvent, which is an alcohol, more preferably, a $C_1$ to $C_4$-alcohol. In other preferred embodiments, the alcohol is methanol, ethanol, n-propanol, iso-propanol, n-butanol, 2-butanol, or 2,2,2-trifluoroethanol ($CF_3CH_2OH$). In a presently preferred embodiment, the alcohol is iso-propanol.

In another exemplary embodiment, the aprotic solvent is an aromatic solvent, a non-aromatic solvent or a mixture thereof. Exemplary aromatic solvents of use in the present invention include toluene, benzene, and xylene, and preferably less toxic aromatic solvents such as toluene and xylene. Exemplary non-aromatic solvents of use in the methods of the invention include tetrahydrofuran (THF), dichloromethane ($CH_2Cl_2$), ethyl acetate (EtOAc), and acetonitrile ($CH_3CN$).

The solvent and substrate are present in essentially any useful ratio. In an exemplary embodiment, the solvent and substrate are present in amounts that provide a substrate solution of from about 0.05 M to about 0.5 M, preferably, from about 0.1 M to about 0.3 M and, more preferably, from about 0.12 M to about 0.34 M.

Amide

The amides formed by the methods of the invention have diverse structures and can include alkyl, heteroalkyl, aryl and heteroaryl substructures. In an exemplary embodiment, the amide has the formula:

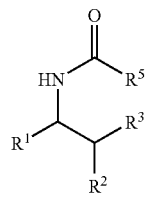

in which $R^1$-$R^3$ and $R^5$ are as discussed above.

As discussed previously, the methods of the invention are useful for preparing amides that include within their structure the 1,2,3,4-tetrahydro-N-alkyl-1-naphthalenamine or 1,2,3,4-tetrahydro-1-naphthalenamine substructure. Thus, in an exemplary embodiment, the amide has the formula:

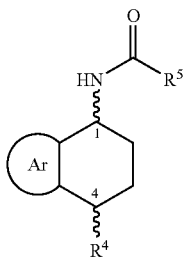

in which $R^4$ and $R^5$ are as described above.

An exemplary amide is a trans amide, having the formula:

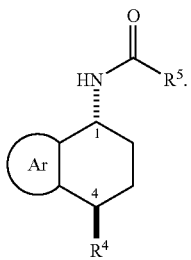

A further exemplary amide has the formula:

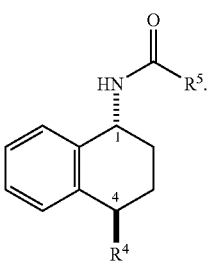

In a preferred embodiment, the amide has the formula:

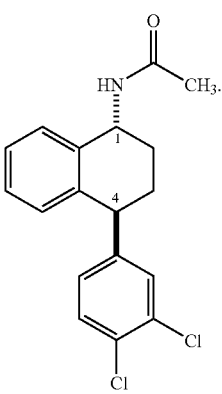

In each of the amide formulae above, C-1 and C-4 have a configuration independently selected from (R) and (S), and in a preferred embodiment, C-1 is of (R)-configuration, and C-4 is of (S)-configuration.

Enantiomeric or Diastereomeric Excess

In a preferred embodiment, the enantiomeric excess (ee) of a desired enantiomer or the diastereomeric excess (de) of a desired diastereomer produced by the present method is from about 60% ee/de to about 99% ee/de, preferably from about 70% ee/de to about 99% ee/de, more preferably, from about 80% ee/de to about 99% ee/de, still more preferably, from about 90% ee/de to about 99% ee/de.

In another preferred embodiment, the invention provides an amide having an enantiomeric or diastereomeric excess of at least about 99%, preferably, at least about 99.4% and, more preferably, at least about 99.8%. Amides that are essentially free of their optical antipodes are accessible through the methods of the invention.

When using rhodium catalyst systems based on chiral bidentate ligands, such as those derived from 1,2-bis(phospholano)ethane (BPE) ligands, P,P-1,2-phenylenebis(7-phosphabicyclo[2.2.1]heptane) (PennPhos) ligands, 5,6-bis(phosphino)bicyclo[2.2.1]hept-2-ene (NorPhos) ligands, or 3,4-bis(phosphino) pyrrolidine (commercially available as catASium® D) ligands, the diastereomeric purity of the trans amide derived from the corresponding enamide is surprisingly high.

In a preferred embodiment, when the amide includes the 1,2,3,4-tetrahydro-N-alkyl-1-naphthalenamine or 1,2,3,4-tetrahydro-1-naphthalenamine subunit, the method provides (1R,4S)-trans amide, which is substantially free of its cis isomer.

In one exemplary embodiment, the enamide is hydrogenated at about 4 to about 6 bar hydrogen pressure using about 0.03 to about 0.05 mol % of a Rh-Me-BPE catalyst in isopropanol, to give the trans N-acetyl amide in about 80 to about 99% de, preferably at least 95% de, and more preferably at least 99% de.

In another exemplary embodiment, the enamide is hydrogenated at about 4 to about 5 bar hydrogen pressure, using about 0.2 to about 0.5 mol % of a Rh-PennPhos catalyst in isopropanol, to give the trans N-acetyl amide in about 80 to about 99% de, preferably at least 95% de, and more preferably at least 99% de.

In yet another exemplary embodiment the enamide is hydrogenated at about 5 to about 8 bar hydrogen pressure, using about 0.01 to about 0.05 mol % of (R,R)N or Phos (COD)RhBF$_4$ catalyst in isopropanol to give the trans N-acetyl amide in about 80-99% de, preferably at least 95% de, and more preferably at least 99% de.

In a preferred embodiment, the hydrogenation is carried out at an enamide concentration of about 0.1 M to about 0.3 M.

In a further exemplary embodiment, the stereoisomerically enriched amide is purified, or further enriched, by selective crystallization. In another exemplary embodiment, the amide is purified, or enriched, to an enantiomeric or diastereomeric purity of about 90 to about 99% ee/de. In another exemplary embodiment, the amide is purified, or enriched, to an enantiomeric or diastereomeric purity of about 95 to about 99% ee/de.

The product of the hydrogenation or hydrogen transfer can be enantiomerically or diastereomerically enriched by methods known in the art, e.g., chiral chromatography, selective crystallization and the like. It is generally preferred that the enrichment afford a product at least about 95% of which is a single stereoisomer. More preferably, at least about 97%, still more preferably at least about 99% is a single stereoisomer.

In a presently preferred embodiment, the enriched trans amide is purified, or enriched, by selective crystallization, affording the desired trans isomer in about 99% de.

C. Amide to Amine

In another aspect, the current invention provides methods for converting an amide formed from the corresponding enamide to an amine. In an exemplary embodiment, the method includes contacting the amide with a deacylating reagent under conditions appropriate to deacylate the amide, thereby forming an amine.

In an exemplary embodiment, the amine has the formula:

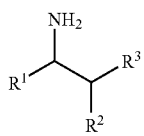

or a salt thereof. The radicals have the identities set forth above.

The amine can be of any desired structure, however, it is preferably a chiral amine. When the amine is chiral, the enantiomeric excess (ee) of a desired enantiomer or the diastereomeric excess (de) of a desired diastereomer produced by the present method is from about 60% ee/de to about 99% ee/de, preferably from about 70% ee/de to about 99% ee/de, more preferably, from about 80% ee/de to about 99% ee/de, still more preferably, from about 90% ee/de to about 99% ee/de.

In another preferred embodiment, the invention provides an amine having an enantiomeric or diastereomeric excess of at least about 99%, preferably, at least about 99.4% and, more preferably, at least about 99.8%. Amines that are essentially free of their optical antipodes are accessible through the methods of the invention.

In an exemplary embodiment, the amine includes the 1,2,3,4-tetrahydro-N-alkyl-1-naphthalenamine or 1,2,3,4-tetrahydro-1-naphthalenamine substructure, and has the formula:

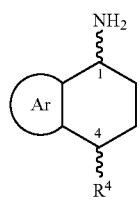

or a salt thereof

In a preferred embodiment, the amine is a trans amine, having the formula:

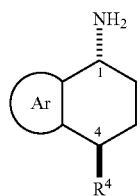

or a salt thereof.

An exemplary amine has the formula:

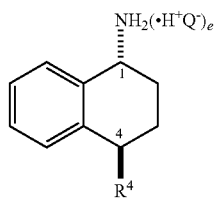

in which Q⁻ is an anion. The index e is a number from 0 to 1. The index may take a fractional value, indicating that the amine salt is a hemi-salt.

In a preferred embodiment, the amine has the formula:

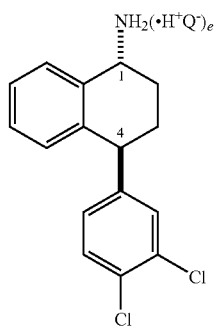

wherein $Q^-$ and e are as described above.

C-1 and C-4 have a configuration independently selected from (R) and (S). Preferably C-1 is of (R)-configuration, and C-4 is of (S)-configuration.

In another preferred embodiment, the amine is in the trans configuration and is substantially free of the cis isomer.

The amide is deacylated by any suitable process. Many methods of deacylating amides to the corresponding amines are known in the art. In an exemplary embodiment, the deacylating reagent is an enzyme. Exemplary enzymes of use in this process include those of the class EC 3.5.1 (e.g., amidase, aminoacylase), and EC 3.4.19.

In another embodiment, the deacylating reagent is an acid or a base. The acid or base can be either inorganic or organic. Mixtures of acids or mixtures of bases are useful as well. When the deacylating reagent is an acid, it is generally preferred that the acid is selected so that the acid hydrolysis produces a product that is a form of the amine. In an exemplary embodiment, the acid is hydrochloric acid (HCl).

Other deacylating conditions of use in the present invention include, but are not limited to, methanesulfonic acid/HBr in alcoholic solvents, triphenylphosphite/halogen (e.g., bromine, chlorine) complex and a di-t-butyl dicarbonate/lithium hydroxide sequence.

In a preferred embodiment, the amide is deacylated by treatment with an activating agent, e.g., trifluoromethanesulfonic anhydride, phosgene, and preferably, oxalyl chloride/pyridine. The reaction is quenched with an alcohol, preferably a glycol, e.g., propylene glycol.

When the amide includes the 1,2,3,4-tetrahydro-N-alkyl-1-naphthalenamine or 1,2,3,4-tetrahydro-1-naphthalenamine substructure, the deacylation conditions preferably are selected such that formation of any dihydronaphthalene side products are minimized.

The amine can be isolated or enriched. A currently preferred method of isolating or enriching the amine includes at least one step of selective crystallization.

The amine is optionally N-alkylated or N-acylated to prepare the corresponding N-alkyl or N-acyl derivative.

In an exemplary embodiment, the invention provides a method suitable for the large scale preparation of trans 4-(3,4-dichlorophenyl)-1,2,3,4-tetrahydro-1-naphthalenamine 5 and salt forms thereof. In an exemplary embodiment, the process involves the synthesis of an enamide, e.g. enamide 3, starting from optically pure (4S)-tetralone 1 via the oxime 2, and subjecting enamide 3 to catalytic asymmetric hydrogenation to afford amide 4, which upon N-deacylation affords trans 4-(3,4-dichlorophenyl)-1,2,3,4-tetrahydro-1-naphthalenamine 5, or a salt thereof (Scheme 2).

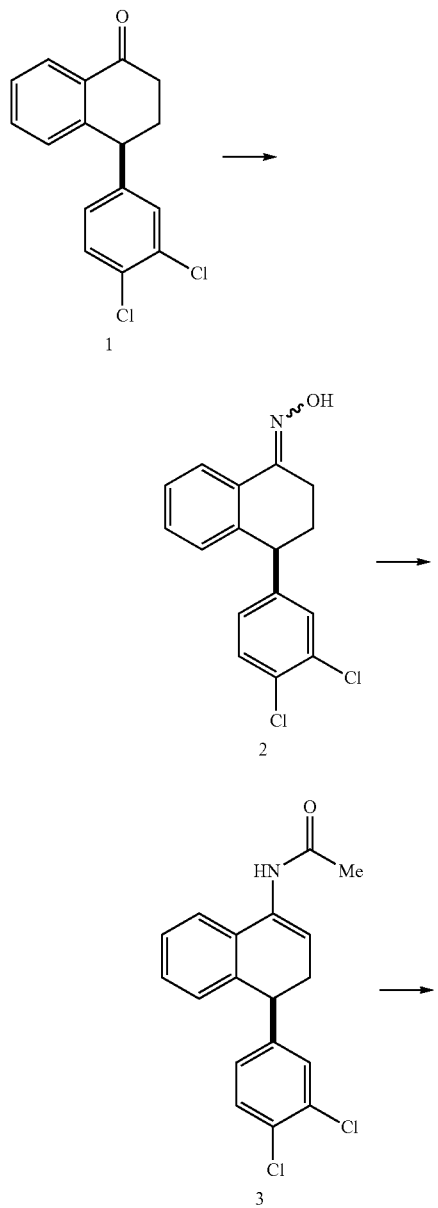

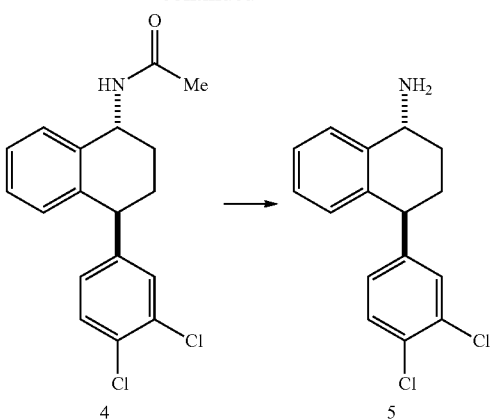

In a preferred embodiment, the compound prepared by the route of Scheme 2 is (1R,4S)-trans 4-(3,4-dichlorophenyl)-1,2,3,4-tetrahydro-1-naphthalenamine. Even more preferred is the preparation of the compound substantially free of its cis isomer.

Compounds according to formula 5 include stereoisomers of desmethylsertraline. The N-methyl analog of 5 is a stereoisomer of sertraline.

The primary clinical use of sertraline is in the treatment of depression. In addition, U.S. Pat. No. 4,981,870 discloses and claims the use of sertraline and related compounds for the treatment of psychoses, psoriasis, rheumatoid arthritis and inflammation.

(1R,4S)-trans 4-(3,4-dichlorophenyl)-1,2,3,4-tetrahydro-1-napthalenamine and (1S,4R)-trans 4-(3,4-dichlorophenyl)-1,2,3,4-tetrahydro-1-napthalenamine are useful in the treatment of CNS-related disorders that are modulated by monoamine activity (U.S. Patent Application No. 2004/0092605 to Jerussi et al.; cited references). Those CNS-related disorders include mood disorders (e.g. depression), anxiety disorders (e.g., OCD), behavioral disorders (e.g. ADD and ADHD), eating disorders, substance abuse disorders and sexual function disorders. Potentially, these molecules produce diminished side effects as compared to the current standards of treatment.

The compounds are also useful for the prophylaxis of migraine.

IV. Compositions

In another aspect, the invention provides a mixture comprising:

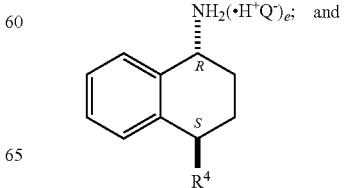

A

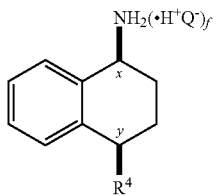

in which R⁴ is a member selected from substituted or unsubstituted aryl and substituted or unsubstituted heteroaryl. Q⁻ is an anion. The indices e and f independently represent a number from 0 to 1. Thus, the structures above encompass hemisalts.

The indices x and y are independently selected from (S) and (R). In one embodiment, when x is (S), y is (S) and when x is (R), y is (R). In another embodiment, when x is (S), y is (R).

In an exemplary embodiment, R⁴ is substituted or unsubstituted aryl. A preferred aryl moiety is a substituted or unsubstituted phenyl moiety.

In another exemplary embodiment, the mixture comprises compounds with the following formulae:

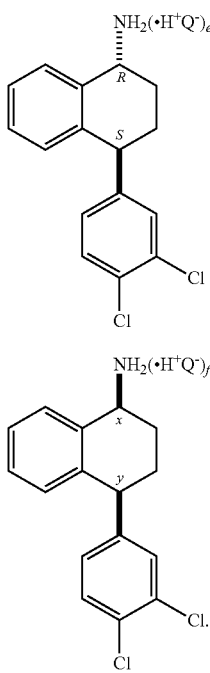

in which e, f, x and y are as described above.

The mixtures set forth above are of use in pharmaceutical formulations. It is generally recognized that stereoisomers of bioactive compounds may have different properties. For example, the S-enantiomer of the beta-adrenergic blocking agent, propranolol, is known to be 100 times more potent than the R-enantiomer. However, potency is not the only concern in the field of pharmaceuticals. Optical purity is important since certain isomers may actually be deleterious rather than simply inert. Mixtures of diastereomers effectively combine and modulate the properties of each of the pure diastereomers. Thus, in selected embodiments, the invention provides mixtures of diastereomeric compounds A and B.

According to the present invention, a therapeutically effective amount of A or B, which may be a pure isomer or a mixture of any A and B, may also be administered to a person in need of therapy.

Disorders treatable with compounds prepared by the methods of the present invention include, but are not limited to, depression, major depressive disorder, bipolar disorder, chronic fatigue disorder, seasonal affective disorder, agoraphobia, generalized anxiety disorder, phobic anxiety, obsessive compulsive disorder (OCD), panic disorder, acute stress disorder, social phobia, fibromyalgia, neuropathic pain, posttraumatic stress disorder, premenstrual syndrome, menopause, perimenopause and male menopause.

In addition to their beneficial therapeutic effects, compounds prepared by methods of the present invention may provide the additional benefit of avoiding or reducing one or more of the adverse effects associated with conventional mood disorder treatments. Such side effects include, for example, insomnia, breast pain, weight gain, extrapyramidal symptoms, elevated serum prolactin levels and sexual dysfunction (including decreased libido, ejaculatory dysfunction and anorgasmia).

The compounds (and their mixtures) prepared by the methods of the present invention are also effective for treating disruptive behavior disorders, such as attention deficit disorder (ADD) and attention deficit/hyperactivity disorder (ADHD), which is in accordance with its accepted meaning in the art, as provided in the DSM-IV-TR™. These disorders are defined as affecting one's behavior resulting in inappropriate actions in learning and social situations. Although most commonly occurring during childhood, disruptive behavior disorders may also occur in adulthood.

The term "treating" when used in connection with the foregoing disorders means amelioration, prevention or relief from the symptoms and/or effects associated with these disorders and includes the prophylactic administration of a compound of formula A or B, a mixture thereof, or a pharmaceutically acceptable salt of either, to substantially diminish the likelihood or seriousness of the condition.

Pure compounds and mixtures prepared by the methods of the present invention are also effective for treating eating disorders. Eating disorders are defined as a disorder of one's appetite or eating habits or of inappropriate somatotype visualization. Eating disorders include, but are not limited to, anorexia nervosa; bulimia nervosa, obesity and cachexia.

Mood disorders, such as depressive disorders, e.g., dysthymic disorder or major depressive disorder; bipolar disorders, e.g., bipolar I disorder, bipolar II disorder, and cyclothymic disorder; mood disorder due to a general medical condition with depressive, and/or manic features; and substance-induced mood disorder can be treated using compounds and mixtures of the invention.

Anxiety disorders, such as acute stress disorder, agoraphobia without history of panic disorder, anxiety disorder due to general medical condition, generalized anxiety disorder, obsessive-compulsive disorder, panic disorder with agoraphobia, panic disorder without agoraphobia, posttraumatic stress disorder, specific phobia, social phobia, and substance-induced anxiety disorder are treatable with compounds and mixtures of the invention.

Compounds and mixtures prepared by methods of the invention are also effective for treating cerebral function disorders. The term cerebral function disorder, as used herein, includes cerebral function disorders involving intellectual deficits, and may be exemplified by senile dementia, Alzheimer's type dementia, memory loss, amnesia/amnestic syndrome, epilepsy, disturbances of consciousness, coma, lowering of attention, speech disorders, Parkinson's disease and autism.

The compounds and mixtures are also of use to treat schizophrenia and other psychotic disorders, such as catatonic, disorganized, paranoid, residual or differentiated schizophrenia; schizophreniform disorder; schizoaffective disorder; delusional disorder; brief psychotic disorder; shared psychotic disorder; psychotic disorder due to a general medical condition with delusions and/or hallucinations.

The compounds of formulae A and B are also effective for treating sexual dysfunction in both males and females. Disorders of this type include, for example, erectile dysfunction and orgasmic dysfunction related to clitoral disturbances.

Compounds and mixtures prepared by the methods of the present invention are also useful in the treatment of substance abuse, including, for example addiction to cocaine, heroin, nicotine, alcohol, anxiolytic and hypnotic drugs, cannabis (marijuana), amphetamines, hallucinogens, phenylcyclidine, volatile solvents, and volatile nitrites. Nicotine addiction includes nicotine addiction of all known forms, such as, for example, nicotine addiction resulting from cigarette, cigar and/or pipe smoking, as well as addiction resulting from tobacco chewing. In this respect, due to their activity as norepinephrine and dopamine uptake inhibitors, the compounds of the present invention can function to reduce the craving for the nicotine stimulus. Bupropion (ZYBAN®, GlaxoSmithKline, Research Triangle Park, N.C., USA) is a compound that has activity at both norepinephrine and dopamine receptors, and is currently available in the United States as an aid to smoking cessation treatment. As a benefit beyond the therapeutic activity of buproprion, however, the compounds of the present invention provide an additional serotonergic component.

Pure compounds and mixtures prepared by the methods of the present invention are also effective in the prophylaxis of migraine.

Compounds and mixtures prepared by the methods of the present invention are also useful in the treatment of pain disorders, including for example fibromyalgia, chronic pain, and neuropathic pain. The term "fibromyalgia" describes several disorders, all characterized by achy pain and stiffness in soft tissues, including muscles, tendons, and ligaments. Various alternative terms for fibromyalgia disorders have been used in the past, including generalized fibromyalgia, primary fibromyalgia syndrome, secondary fibromyalgia syndrome, localized fibromyalgia, and myofascial pain syndrome. Previously, these disorders were collectively called fibrositis or fibromyositis syndromes. Neuropathic pain disorders are thought to be caused by abnormalities in the nerves, spinal cord, or brain, and include, but are not limited to: burning and tingling sensations, hypersensitivity to touch and cold, phantom limb pain, postherpetic neuralgia, and chronic pain syndrome (including, e.g., reflex sympathetic dystrophy and causalgia).

The magnitude of a prophylactic or therapeutic dose of a compound of formulae A, B or mixtures thereof will vary with the nature and severity of the condition to be treated and the route of administration. The dose, and perhaps the dose frequency, will also vary according to the age, body weight and response of the individual patient. In general, the total daily dose ranges of compounds of the present invention will be from about 1 mg per day to about 500 mg per day, preferably about 1 mg per day to about 200 mg per day, in single or divided doses. Dosages of less than 1 mg per day of compounds of the invention are also within the scope of the instant invention.

Any suitable route of administration may be employed. For example, oral, rectal, intranasal, and parenteral (including subcutaneous, intramuscular, and intravenous) routes may be employed. Dosage forms can include tablets, troches, dispersions, suspensions, solutions, capsules and patches.

Pharmaceutical compositions of the present invention include as active ingredient, a single compound, or a mixture of compounds, of formula A or B, or a pharmaceutically acceptable salt of A or B, together with a pharmaceutically acceptable carrier and, optionally, with other therapeutic ingredients.

The pharmaceutically acceptable carrier may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets, with the solid oral preparation being preferred over the liquid preparations. Preferred solid oral preparations are tablets or capsules, because of their ease of administration. If desired, tablets may be coated by standard aqueous or nonaqueous techniques. Oral and parenteral sustained release dosage forms may also be used.

Exemplary formulations, are well known to those skilled in the art, and general methods for preparing them are found in any standard pharmacy school textbook, for example, Remington, THE SCIENCE AND PRACTICE OF PHARMACY, 21 st Ed., Lippincott.

Thus, as set forth herein, the invention is exemplified by the following aspects and embodiments.

A method for converting an oxime into an enamide. The method includes, (a) contacting the oxime with a phosphine and an acyl donor, under conditions appropriate to convert the oxime into the enamide.

The method according to the preceding paragraph in which the oxime has the formula:

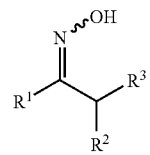

wherein $R^1$, $R^2$ and $R^3$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl. At least two of $R^1$, $R^2$ and $R^3$ are optionally joined to form a ring system selected from substituted or unsubstituted cycloalkyl, substituted or unsubstituted heterocycloalkyl, substituted or unsubstituted aryl and substituted or unsubstituted heteroaryl.

The method of any of the preceding paragraphs in which the oxime has the formula:

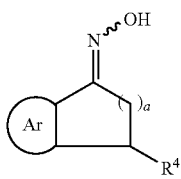

wherein Ar is a member selected from substituted or unsubstituted aryl and substituted or unsubstituted heteroaryl. $R^4$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and, the index a is selected from the integers from 1 to 4.

The method of any of the preceding paragraphs in which $R^4$ is substituted or unsubstituted aryl.

The method of any of the preceding paragraphs in which $R^4$ is substituted or unsubstituted phenyl.

The method of any of the preceding paragraphs in which $R^4$ is phenyl substituted with at least one halogen.

The method of any of the preceding paragraphs in which $R^4$ has the formula:

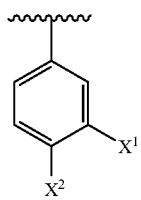

wherein $X^1$ and $X^2$ are independently selected halo moieties.

The method of any of the preceding paragraphs in which $X^1$ and $X^2$ are each chloro.

The method of any of the preceding paragraphs in which Ar is substituted or unsubstituted phenyl.

The method of any of the preceding paragraphs in which the oxime has the formula:

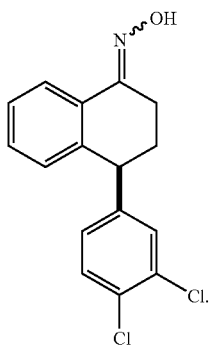

The method of any of the preceding paragraphs in which acyl donor has the formula: Z—C(O)—$R^5$, wherein Z is a leaving group. $R^5$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

The method according any of the preceding paragraphs in which Z has the formula:

$R^6$—C(O)—O— wherein $R^6$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

The method according to any of the preceding paragraphs in which both $R^5$ and $R^6$ are independently selected substituted or unsubstituted $C_1$-$C_4$ moieties.

The method according to any of the preceding paragraphs in which the phosphine has the formula:

$P(Q)_3$ wherein each Q is a member independently selected from H, substituted or unsubstituted alkyl and substituted or unsubstituted aryl.

The method according to any of the preceding paragraphs in which each Q is a member independently selected from substituted or unsubstituted $C_1$-$C_6$ alkyl.

The method according to any of the preceding paragraphs in which the contacting is in solution with an aprotic solvent.

The method according to any of the preceding paragraphs in which the aprotic solvent is an aromatic solvent.

The method according to any of the preceding paragraphs in which the aprotic aromatic solvent is selected from toluene, xylene and combinations thereof.

The method according to any of the preceding paragraphs in which enamide has the formula:

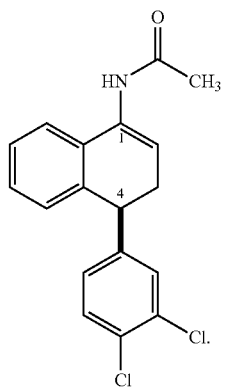

The method according to any of the preceding paragraphs in which C-4 has a configuration selected from R, S and mixtures thereof.

The method according to any of the preceding paragraphs in which C-4 is of S configuration.

The method according to any of the preceding paragraphs further including: (b) contacting the enamide formed in step (a) with a hydrogenation catalyst and hydrogen or hydrogen transfer reagent under conditions appropriate to hydrogenate a carbon-carbon double bond of the enamide, thereby converting the enamide to an amide.

The method according to any of the preceding paragraphs in which the catalyst is a chiral catalyst.

The method according to any of the preceding paragraphs in which the chiral catalyst is a complex of a transition metal with a chiral phosphine ligand.

The method according to any of the preceding paragraphs in which the amide is a racemic or chiral amide.

The method according to any of the preceding paragraphs in which amide has the formula:

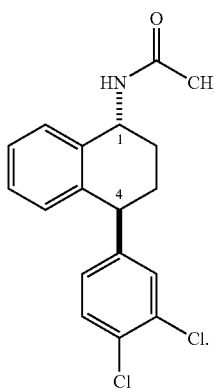

The method according to any of the preceding paragraphs in which C-1 and C-4 have a configuration independently selected from R and S.

The method according to any of the preceding paragraphs in which C-1 is of R configuration; and C-4 is of S configuration.

The method according to any of the preceding paragraphs further including: (c) contacting the amide with a deacylating reagent under conditions appropriate to deacylate —HNC(O)$R^5$ of the amide, thereby forming an amine.

The method according to any of the preceding paragraphs including: (d) isolating said amine.

The method according to any of the preceding paragraphs in which isolating comprises selective crystallization.

The method according to any of the preceding paragraphs in which the amine has the formula:

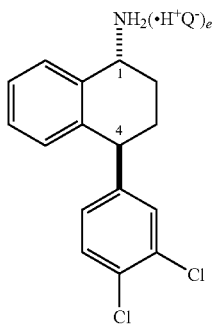

wherein $Q^-$ is an anion; and e is 0 to 1.

The method according to any of the preceding claims in which C-1 and C-4 have a configuration independently selected from R and S.

The method according to any preceding claims in which C-1 is of R configuration; and C-4 is of S configuration.

A method of converting an oxime having the formula

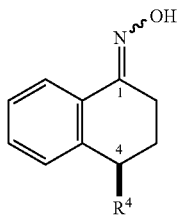

into an enamide having the formula:

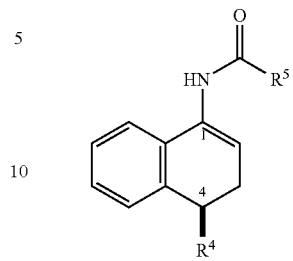

wherein $R^4$ is selected from substituted or unsubstituted aryl and substituted or unsubstituted heteroaryl. $R^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl. The method includes: (a) contacting the oxime with a phosphine and an acyl donor under conditions appropriate to convert the oxime to the enamide.

The method according to the preceding paragraph in which C-4 is of S configuration.

The method according to the preceding paragraphs in which the phosphine is a trialkylphosphine.

The method according to the preceding paragraphs in which the oxime, the acyl donor and the phosphine are dissolved in an aromatic solvent.

The method according to the preceding paragraphs in which the acyl donor is an alkyl anhydride.

The method according to the preceding paragraphs including: (b) contacting the enamide formed in step (a) with a chiral hydrogenation catalyst and hydrogen under conditions appropriate to hydrogenate a carbon-carbon double bond conjugated to C(O) of the enamide, thereby converting the enamide to an amide having the formula:

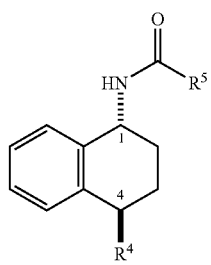

wherein C-1 has a configuration selected from R and S.

The method according to the preceding paragraphs in which the chiral catalyst includes rhodium complexed to a chiral phosphine ligand.

The method according to the preceding paragraphs further including: (c) contacting the amide with a deacylating reagent under conditions appropriate to deacylate —HNC(O)$R^5$ of the amide, thereby forming an amine having the formula:

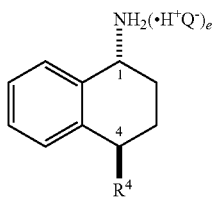

wherein Q⁻ is an anion. The index e is 0 or 1.

The method according to the preceding paragraphs in which the deacylating reagent is an enzyme.

The method according to the preceding paragraphs in which the deacylating reagent is an acid.

A mixture comprising:

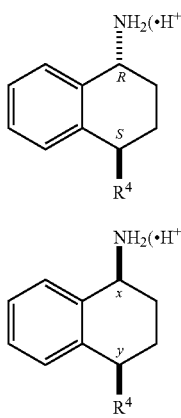

wherein $R^4$ is a member selected from substituted or unsubstituted aryl and substituted or unsubstituted heteroaryl. Q⁻ is an anion. The indices e and f are independently selected numbers from 0 to 1; and x and y are selected from R and S, such that when x is R, y is R, and when x is S, y is S.

The mixture according to the preceding paragraph in which A is present in the mixture in a diastereomeric excess of at least 90% relative to B.

The mixture according to the preceding paragraphs in which A is present in said mixture in a diastereomeric excess of at least 98% relative to B.

The mixture according to the preceding paragraphs in which x and y are R.

The mixture according to the preceding paragraphs in which x and y are S.

The mixture according to the preceding paragraphs in which $R^4$ is substituted or unsubstituted phenyl.

A pharmaceutical formulation including a mixture according to the preceding paragraphs.

The following examples are provided to illustrate selected embodiments of the invention and are not to be construed as limiting its scope.

EXAMPLES

Example 1

Synthesis of N-((S)-4-(3,4-dichlorophenyl)-3,4-dihydronaphthalen-1-yl)acetamide (3)

1.1. Synthesis of Oxime 2

A suspension formed from a mixture of (S)-tetralone 1 (56.0 g, 0.192 mol), hydroxylamine hydrochloride (14.7 g, 0.212 mol), and sodium acetate (17.4 g, 0.212 mol) in methanol (168 mL) was heated to reflux for 1 to 5 hours under a $N_2$ atmosphere. The progress of the reaction was monitored by HPLC. After the reaction was complete, the reaction mixture was concentrated in vacuo. The residue was diluted with toluene (400 mL) and 200 mL water. The organic layer was separated and washed with an additional 200 mL water. The organic layer was concentrated and dried to give crude solid oxime 2 (58.9 g, 100%), m. p. 117-120° C.

¹H NMR (400 MHz, CDCl₃) δ (ppm) 9.17 (br, 1H, OH), 7.98 (m, 1H), 7.36 (d, 1H, J=8.0 Hz), 7.29 (m, 2H), 7.20 (d, 1H, J=2.4 Hz), 6.91 (m, 2H), 4.11 (dd, 1H, J=7.2 Hz, 4.4 Hz), 2.82 (m, 2H), 2.21 (m, 1H), 2.08 (m, 1H). ¹³C NMR (100 MHz, CDCl₃) δ 154.94, 144.41, 140.40, 132.83, 130.92, 130.82, 130.68, 130.64, 129.98, 129.38, 128.12, 127.64, 124.48, 44.52, 29.51, 21.27.

1.2. Synthesis of Enamide 3

The solution of the crude oxime 2 (59 g, 0.193 mol) in toluene (500 mL) was purged with $N_2$ for 30 min. $Et_3P$ (25 g, 0.212 mol) was charged. After stirring for 10 min, acetic anhydride (21.6 g, 20 mL, 0.212 mol) was added. The reaction mixture was refluxed for 8 to 13 h. Progress of the reaction was monitored by HPLC. The reaction mixture was cooled to room temperature. 6N NaOH (aq) (86 mL, 0.516 mol) and 1.0 M (n-Bu)₄NOH in methanol (1.0 mL) were added. The hydrolysis was complete in about 2 to 4 h. The organic layer was separated and diluted with EtOAc (300 mL) and 2-BuOH (30 mL). The diluted organic solution was washed with 1% HOAc (aq) solution (300 mL) and DI water (3×300 mL) and concentrated to about 350 mL of a slurry in vacuo. The slurry was diluted with heptane (100 mL) and 2-BuOH (4 mL) and heated to reflux to form a clear solution. Heptane (50 to 200 mL) was slowly added until a cloudy solution formed. The suspension was slowly cooled to rt. The product was filtered out, washed with 30% toluene and 70% heptane (3×100 mL) solution and dried in a vacuum oven to give 56.9 g white solid (enamide 3, 89% yield), m. p. 167-168° C.

(S)-Tetralone 1 (50.0 g, 0.172 mol) was slurried in methanol (150 mL) with hydroxylamine hydrochloride (13.1 g, 0.189 mol) and sodium acetate (15.5 g, 0.189 mol). The resulting suspension was heated to reflux for 2 to 6 h under an inert atmosphere with progress monitored by HPLC. On completion, the mixture was cooled to 25° C., diluted with toluene (300 mL) and quenched with 1.7 N NaOH (100 mL). The mixture was concentrated in vacuo under reduced pressure, the aqueous layer removed and the organic layer washed further with DI water (100 mL). Further toluene (300 mL) was charged to the vessel and water removed by azeotropic distillation. Once at ambient temperature, n-Bu₃P (47.1 mL, 0.183 mol) was charged to the reactor, followed by acetic anhydride (32.5 mL, 0.344 mol). The reaction was heated to reflux and monitored by HPLC. After 20-24 h, the reaction was cooled to ambient temperature and quenched with 6 N NaOH (120 mL). This mixture was allowed to react for 2 to 6 h before the aqueous layer was removed. The organic phase was washed with DI water (100 mL). Concentration of the mixture in vacuo, cooling to room temperature and diluting with isopropanol (50 mL) was done prior to addition of heptane to assist with crystallization. An initial charge of heptane (50 mL) was followed by an additional 650 mL. Aging of the slurry followed by filtration, washing (4×100 mL heptane) and drying yielded a light yellow solid (enamide 3, 44.1 g, 77%).

¹H NMR (400 MHz, CDCl₃) δ (ppm) 7.35 (d, 1H, J=8.4 Hz), 7.26 (m, 3H), 7.17 (m, 1H), 7.05 (dd, 1H, J=8.0, 1.6 Hz), 7.00 (br, 1H), 6.87 (m, 0.82H, 82% NH rotamer), 6.80 (br, 0.18H, 18% NH rotamer), 6.31 (t, 0.82H, J=4.8 Hz, 82% H rotamer), 5.91 (br, 0.18H, 18% H rotamer), 4.12 (br, 0.18H, 18% H rotamer), 4.03 (t, 0.82H, J=8.0 Hz, 82% H rotamer), 2.72 (m, 1H), 2.61 (ddd, 1H, J=16.8, 8.0, 4.8 Hz), 2.17 (s, 2.46H, 82% CH$_3$ rotamer), 1.95 (s, 0.54H, 18% CH$_3$ rotamer). 100 MHz $^{13}$CNMR (CDCl$_3$) δ 169.3, 143.8, 137.7, 132.3, 131.8, 131.4, 130.5, 130.3, 130.2, 128.8, 128.1, 127.8, 127.2, 123.8, 122.5, 121.2, 117.5, 42.6, 30.3, 24.1.

Example 2

Synthesis of N-((1R,4S)-4-(3,4-dichlorophenyl)-1,2,3,4-tetrahydronaphthalen-1-yl)acetamide (4)

The enamide 3 (24 g, 72 mmol) was slurried in degassed isopropanol (200 mL). The resulting slurry was transferred to the appropriate reactor. Prior to the addition of the catalyst solution, the content of the reactor was purged with nitrogen. A solution of (R,R)-MeBPE(COD)RhBF$_4$ catalyst (20.1 mg, 0.036 mmol, 0.05 mol %) in isopropanol (IPA) (100 mL) was added to the reactor. The content was cooled to 0° C. and purged with nitrogen three times. The reactor was then purged with hydrogen and pressurized to 90 psig. The reaction was aged with agitation at 0° C. for 7.5 h and conversion was monitored by the hydrogen uptake. The content was then warmed to RT and hydrogen was vented. After purging with nitrogen, the contents were drained. The reaction mixture was heated to 50° C. and filtered through a pad of Celite. The clear orange solution was concentrated to ~50% volume (150 mL) and diluted with toluene (5.9 g, 5 wt %). The suspension was heated to 65° C. and water (14.7 mL) was added dropwise to form a cloudy solution. The slurry was slowly cooled to −10° C. and aged for 30 minutes. The solid was filtered and washed with cold IPA (2×45 mL). The cake was dried under vacuum at 45° C. overnight to afford 20.0 g (83% yield) of trans acetamide 4 (>99% de).

$^1$H NMR (CDCl$_3$) 400 MHz δ 7.34 (dd, 2H, J=7.9, 2.4 Hz), 7.23 (t, 1H, J=7.5 Hz), 7.15 (m, 2H), 6.85 (dd, 1H, J=8.2, 2.0 Hz), 6.82 (d, 1H, J=7.7 Hz), 5.72 (d, 1H, J=8.4 Hz), 5.31 (dd, 1H, J=13.2, 8.1 Hz), 4.10 (dd, 1H, J=7.0, 5.9 Hz), 2.17 (m, 2H), 2.06 (s, 3H), 1.87 (m, 1H). 1.72 (m, 1H); $^{13}$C NMR (CDCl$_3$) 100 MHz δ 169.7, 146.9, 138.8, 137.7, 132.6, 130.8, 130.6, 130.5, 130.3, 128.4, 128.3, 127.9, 127.4, 47.9, 44.9, 30.5, 28.4, 23.8.

Example 3

Synthesis of (1R,4S)-4-(3,4-dichlorophenyl)-1,2,3,4-tetrahydronaphthalen-1-amine Hydrochloride (5)

A solution of trans-acetamide 4 (9.0 g, 26.9 mmol), n-propanol (45 mL) and 5M hydrochloric acid (45 mL) was refluxed for approximately 48 h (90-93° C.). During this time, the reaction temperature was maintained at ≧90° C. by periodically collecting the distillate until the reaction temperature was >92° C. Additional n-propanol was added periodically to maintain the solution at its original volume. After the hydrolysis was complete, the solution was slowly cooled to 0° C., resulting in a slurry, which was aged for one hour at 0° C. The reaction mixture was filtered, and the cake was washed with 1:1 methanol/water (20 mL), followed by t-butyl methyl ether (20 mL). The wet-cake was dried under vacuum at 45 to 50° C. to afford 7.0 g of the amine hydrochloride 5 (80% yield).

$^1$H NMR (DMSO-d$_6$) δ 1.81-1.93 (m, 2H), 2.12-2.21 (m, 1H), 2.28-2.36 (m, 1H), 4.28 (t, 1H, J=6.8), 4.59 (br.s, 1H), 6.84 (d, 1H, J=7.6), 7.05 (dd, 1H, J=8.4, 1.6), 7.25 (t, 1H, J=7.6), 7.32 (t, 1H, J=7.6), 7.37 (d, 1H, J=1.6), 7.56 (d, 1H, J=8.4), 7.76 (d, 1H, J=7.2), 8.80 (br.s, 3H); $^{13}$C NMR (DMSO-d$_6$) 147.4, 138.9, 133.6, 131.0, 130.5, 130.4, 130.1, 129.0, 128.9, 128.4, 128.2, 126.8, 47.9, 43.1, 27.8, 25.2.

Example 4

In Situ Formation/Acylation of Oxime

Oxime 2 was acylated in situ to afford the intermediate 2A, which undergoes reductive acylation to provide a mixture of the acylated enamide 3 and the diacylated analog 3A. The reaction was carried out in either toluene or o-xylene at reflux. The mixture of 3 and 3A was then treated with an aqueous solution of base such as sodium hydroxide or sodium carbonate, with or without a phase transfer catalyst (e.g. tetrabutylammonium hydrogen sulfate/hydroxide), to convert the intermediate 3A to the desired enamide 3. Exemplary reaction conditions for the conversion of oxime 2 to enamide 3 are shown in Schemes 3a and 3b.

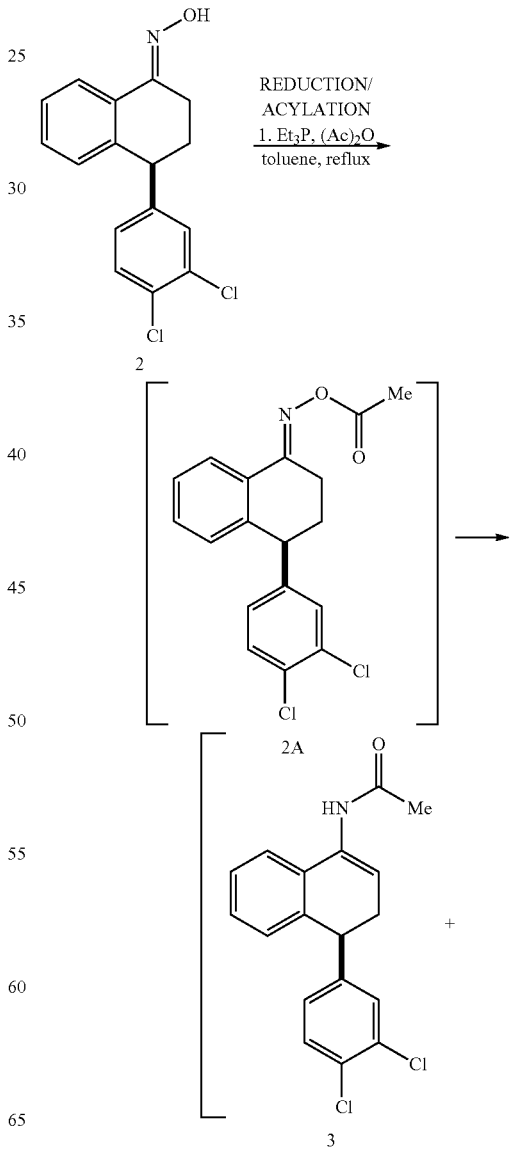

Scheme 3a

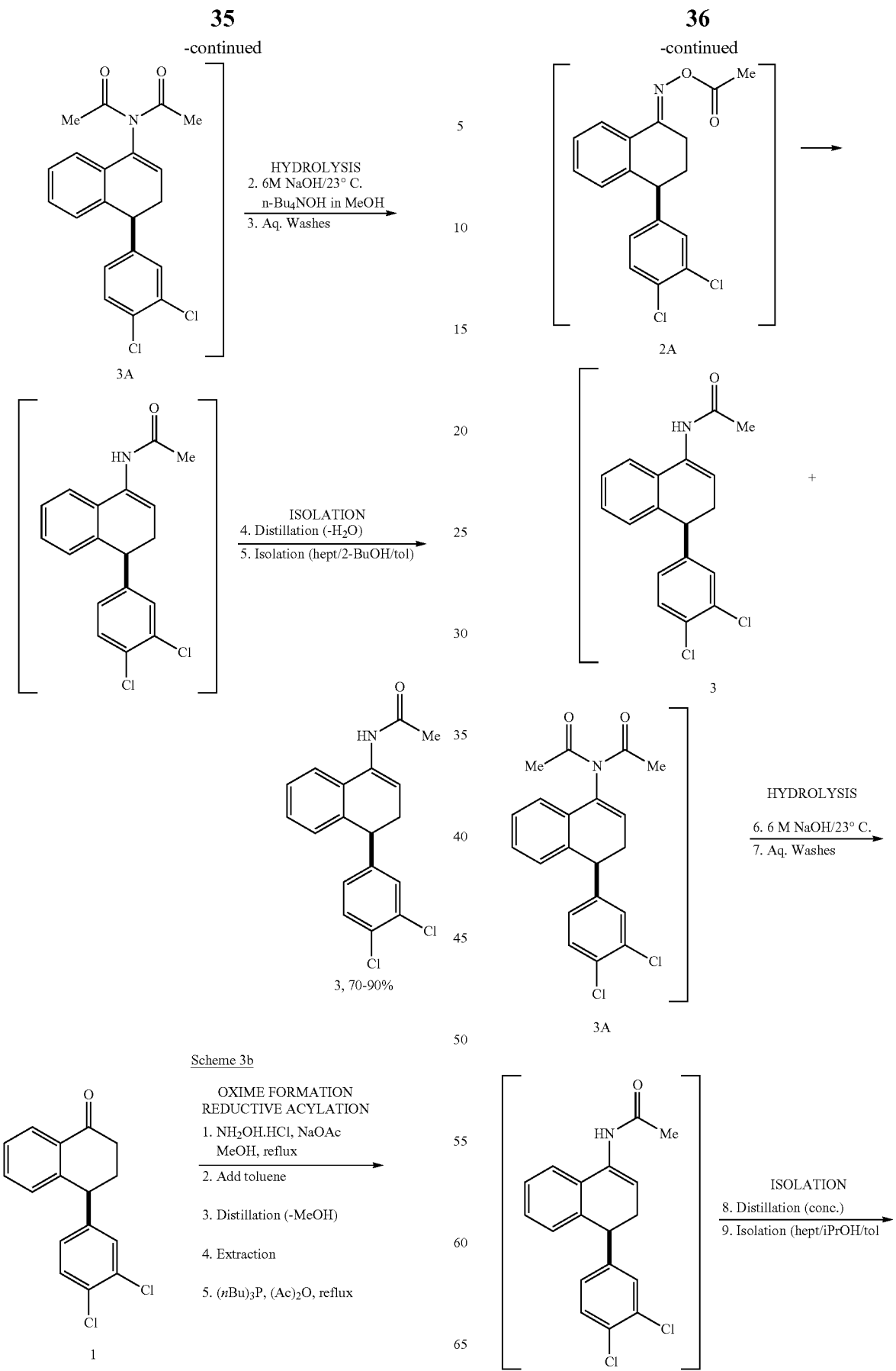

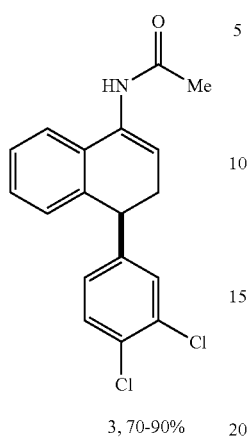

3, 70-90%

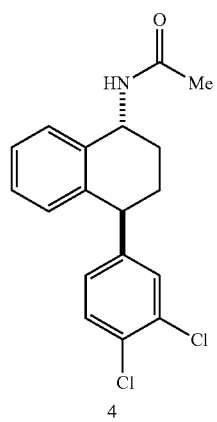

4

Example 5

Catalytic Asymmetric Hydrogenation of the Enamide 3 Using (R,S,R,S)-MePenn Phos(COD)RhBF$_4$ as the Catalyst As shown in Scheme 4, the enamide 3 was subjected to homogeneous catalytic asymmetric hydrogenation in the presence of a chiral catalyst, H$_2$, and a solvent. In this example the catalyst was derived from the complex of the transition metal rhodium with the chiral phosphine ligand, (1R,2S,4R,5S)—P,P-1,2-phenylenebis {(2,5-endo-dimethyl)-7-phosphabicyclo[2.2.1]heptane}(R,S,R,S-MePennPhos). The hydrogenations were carried out at a substrate concentration of about 0.12 M to about 0.24 M of compound 3.

Example 6

Catalytic Asymmetric Hydrogenation of the Enamide 3 Using (R,R)-MeBPE Rh(COD)BF$_4$ as the Catalyst As shown in Scheme 5, the enamide 3 was subjected to homogeneous catalytic asymmetric hydrogenation in the presence of a chiral catalyst, H$_2$, and a solvent. In this example the catalyst was derived from the complex of the transition metal rhodium with the chiral phosphine ligand, (R,R)-1,2-bis(2,5-dimethylphospholano)ethane (R,R-MeBPE). The hydrogenations were carried out in the concentration range of about 0.12 M to about 0.24 M relative to the substrate 3.

Scheme 4

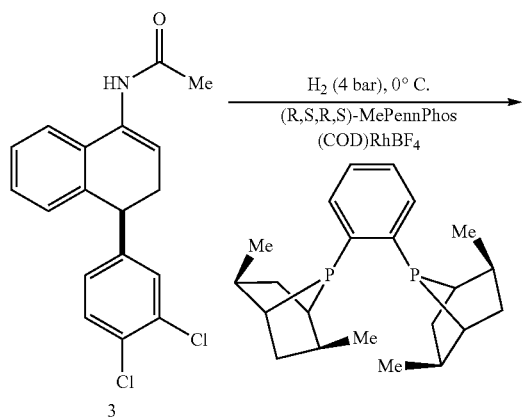

Scheme 5

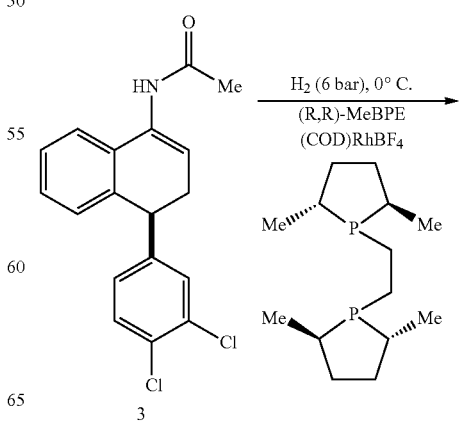

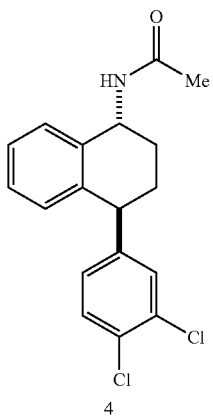

4

Example 7

Asymmetric Hydrogenation Catalyzed by (R,R)-Norphos(COD)RH—BF$_4$

A slurry of the (S)-enacetamide, N-((S)-4-(3,4-dichloropheyl)-3,4-dihydronaththalen-1-yl)acetamide (60.4 g, 0.18 mol), in isopropanol (595.0 g) was purged of oxygen with vacuum/nitrogen cycles. The homogeneous catalyst precursor (referred to as a "catalyst"), (R,R)-Norphos(COD)RH—BF$_4$ was added as a solution in methanol (34.6 mg, 0.025 mol %, 0.53 mL). After purging the system with hydrogen several times, the vessel was filled with hydrogen at the desired reaction pressure (approx 7 bar). The mixture was stirred at 25° C. and reaction progress was monitored by hydrogen uptake. Once the reaction was judged to be complete (hydrogen uptake and HPLC), the pressure was released and the system was purged repeatedly with nitrogen. The light yellow slurry was diluted with isopropanol (194.7 g), heated to dissolution (65° C.) and polish filtered. The mixture was heated to reflux to dissolve all solids. The solution was slowly cooled to 60-65° C. at which time the product crystallized. The antisolvent, water (262 g), was added at about 60-65° C., then the mixture was cooled to 0° C. over two hours and held at that temperature for aging. Filtration of the lightly colored solid was followed by washing with cold isopropanol (2×61 g). Drying of the off white solid under reduced pressure at 50-55° C. provided the (1R,4S)-acetamide in 99% de (56.6 g, 93% yield).

Example 8

Oxime and Enamide Formation

Chiral (4S)-tetralone (100.0 g, 0.34 mol) was reacted with hydroxylamine hydrochloride (28.7 g, 0.41 mol) and sodium acetate (33.8 g, 0.41 mol) in toluene (1.37 L) for approximately 2 h at 103° C. Water was removed from the reaction mixture by azeotropic distillation. The reaction was quencher at 25° C. with 2 N sodium hydroxide (167.0 g). The aqueous phase was separated and the organic phase was washed once with water (400.0 g). Toluene (700.0 g) was added was added and the resulting organic solution, containing the oxime, was dried by azeotropic distillation under reduced pressure to the desired reaction concentration. Triethylphosphine (89.0 g, 0.38 mol, 50 wt % in toluene) is added, followed by addition of acetic anhydride (38.5 g, 0.38 mol), which afforded the oxime acetate intermediate. The reaction mixture was allowed to react at reflux (112-113° C.) until the remaining oxime acetate is <2% of the product, as determined by HPLC. The reaction mixture was cooled to 20-25° C. and the minor enimide by-product was hydrolyzed (to enacetamide) using 6 N sodium hydroxide (210 g) in conjunction with the phase transfer reagent, tertbutylammonium hydroxide (5.0 g). The biphasic mixture was allowed to phase separate and the aqueous phase was discarded. The organic phase was washed with 0.5% acetic acid aqueous solution (67° C., 600.0 g). The aqueous phase was removed and the organic phase was washed once with water (67° C., 600.0 g) to remove inorganic salts. The organic phase was concentrated and the warm solution was polish filtered to remove additional inorganic salts. Heptanes (150 g) and 2-butanol (7.0 g) were added and the slurry was heated to 100° C. in order to achieve dissolution. The solution was cooled to approximately 85° C. to initiate crystallization. Additional heptanes (190 g) were added to the slurry at 85° C., and the mixture was then cooled to 0° C. The slurry was aged at 0° C. for 15 min., then filtered and washed three times with a solution consisting of a mixture of heptanes and toluene (125 g). The product was vacuum dried at 35-45° C. 17.8 g (89% yield) of a white crystalline solid, (S)-enacetamide was recovered.

The method according to this example was applied to a number of substrates, the results of which are set forth in Table 1.

TABLE 1

| | Oximes and Enamides Produced | | |
|---|---|---|---|
| Entry | Oxime, yield | Enamide reaction time | Enamide, yield |
| 1 | NOH<br>Quantitative | 16.5 h | 89% |

TABLE 1-continued
Oximes and Enamides Produced
| Entry | Oxime, yield | Enamide reaction time | Enamide, yield |
|---|---|---|---|
| 2 | 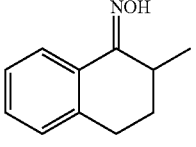<br>Quantitative | 22 h | 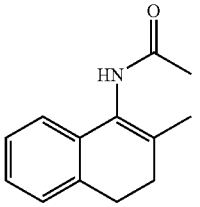<br>74% |
| 3 | 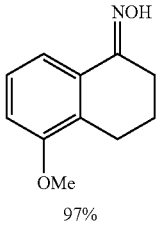<br>97% | 23 h | 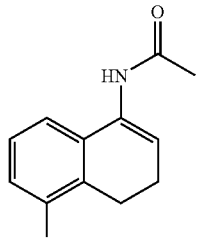<br>77% |
| 4 | 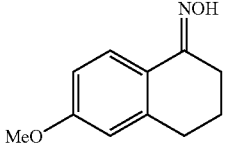<br>96% | 19 h | 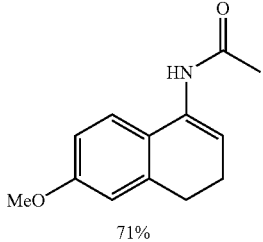<br>71% |
| 5 | 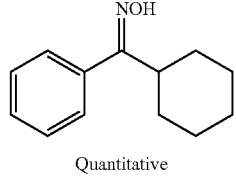<br>Quantitative | 24 h | 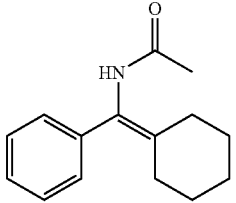<br>90% |
| 6 | 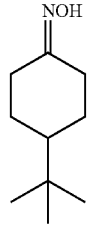<br>99.8% | 21.5 h | 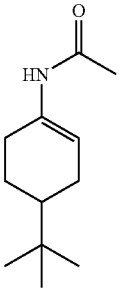<br>71% |

TABLE 1-continued
Oximes and Enamides Produced
| Entry | Oxime, yield | Enamide reaction time | Enamide, yield |
|---|---|---|---|
| 7 | 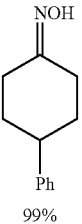 99% | 21.5 h | 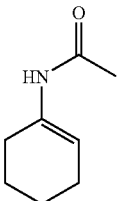 64% |
| 8 | 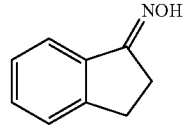 93% | 1.5 h | 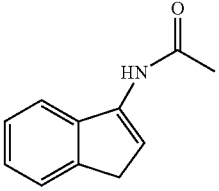 78% |
| 9 | 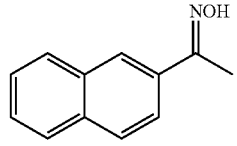 Quantitative | 10 h | 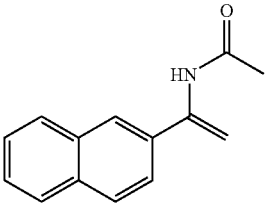 76% |
| 10 | 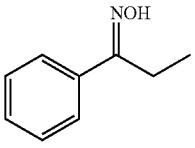 Quantitative | 10 h | 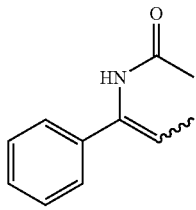 58% |
| 11 | 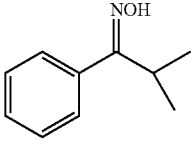 99% | 22.5 h | 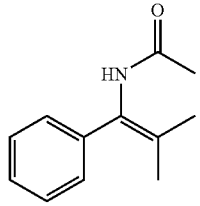 58% |

TABLE 1-continued

Oximes and Enamides Produced

| Entry | Oxime, yield | Enamide reaction time | Enamide, yield |
|---|---|---|---|
| 12 | 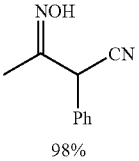 98% | 28 h | 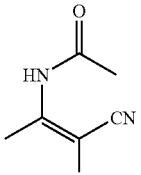 54% |
| 13 | 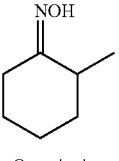 Quantitative | <22 h | 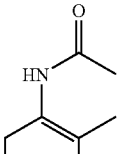 54% |

Example 9

Amide Deprotection

A solution of (1R,4S)-acetamide in dry THF (212.7 g, 239.3 mL) was treated with dry pyridine (8.7 g, 8.9 mL, 110 mmol). The resulting clear, colorless solution was cooled to approximately 0° C. Oxalyl chloride (12.9 g, 8.9 mL, 101.6 mmol) was added dropwise to the stirred solution, with care to control the exotherm and effervescence of CO and $CO_2$. The addition of the activating reagent was accompanied by the formation of a slurry. The slurry was allowed to stir cold for a short period (approx. 15 min) prior to sampling for conversion assessment. Once the reaction was complete, dry propylene glycol was added to the reaction, resulting in a minor exotherm. The reaction was warmed to 25° C., during which time the slurry changed in color and consistency. HPLC analysis of a second sample showed completion before the addition of 1-propanol (96.9 g, 120.5 mL). 6N HCl (128.0 g, 120.0 mL) was added. The mixture was heated to effect dissolution and the resulting mixture was polish filtered. THF was removed by atmospheric distillation. After concentration of the mixture, it was slowly cooled to 3° C. The resulting lightly colored slurry was filtered to yield and off-white cake. The cake was first washed with 17 wt % n-PrOH in deionized water (72.6 g, 75 mL total) and then with cold mtBE (55.5 g, 75 mL). The off-white wet cake was dried under vacuum at 45-50° C. The product was recovered as an off-white to white solid (24.8 g, 84.1% yield) with excellent purity (>99% purity by HPLC).

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A method for converting an oxime into an enamide, said method comprising:
   (a) contacting said oxime with a phosphine and an acyl donor, under conditions appropriate to convert said oxime into said enamide.

2. The method according to claim 1 wherein said oxime has the formula:

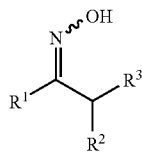

wherein
$R^1$, $R^2$ and $R^3$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and
at least two of $R^1$, $R^2$ and $R^3$ are optionally joined to form a ring system selected from substituted or unsubstituted cycloalkyl, substituted or unsubstituted heterocycloalkyl, substituted or unsubstituted aryl and substituted or unsubstituted heteroaryl.

3. The method according to claim 1, wherein said oxime has the formula:

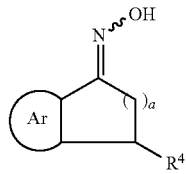

wherein
- Ar is a member selected from substituted or unsubstituted aryl and substituted or unsubstituted heteroaryl;
- $R^4$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl; and
- a is selected from the integers from 1 to 4.

4. The method according to claim 3 wherein $R^4$ is substituted or unsubstituted aryl.

5. The method according to claim 4 wherein $R^4$ is substituted or unsubstituted phenyl.

6. The method according to claim 5 wherein $R^4$ is phenyl substituted with at least one halogen.

7. The method according to claim 6 wherein $R^4$ has the formula:

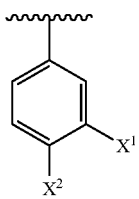

wherein
- $X^1$ and $X^2$ are independently selected halo moieties.

8. The method according to claim 7 wherein $X^1$ and $X^2$ are each chloro.

9. The method according to claim 3 wherein Ar is substituted or unsubstituted phenyl.

10. The method according to claim 9, said oxime having the formula:

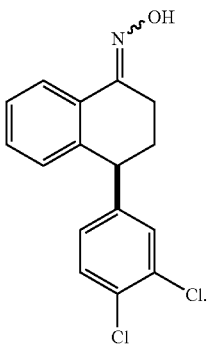

11. The method according to claim 1 wherein said acyl donor has the formula:

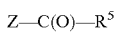

wherein
- Z is a leaving group; and
- $R^5$ is a member selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

12. The method according to claim 11 wherein Z has the formula:

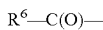

wherein
- $R^6$ is a member selected from substituted or unsubstituted alkyl, substituted or unsubstituted heteroalkyl, substituted or unsubstituted aryl, substituted or unsubstituted heteroaryl and substituted or unsubstituted heterocycloalkyl.

13. The method according to claim 12 wherein both $R^5$ and $R^6$ are independently selected substituted or unsubstituted $C_1$-$C_4$ moieties.

14. The method according to claim 1 wherein said phosphine has the formula:

wherein
- each Q is a member independently selected from H, substituted or unsubstituted alkyl and substituted or unsubstituted aryl.

15. The method according to claim 14 wherein each Q is a member independently selected from substituted or unsubstituted $C_1$-$C_6$ alkyl.

16. The method according to claim 1 wherein said contacting is in solution with an aprotic solvent.

17. The method according to claim 16 wherein said aprotic solvent is an aromatic solvent.

18. The method according to claim 17 wherein said aprotic aromatic solvent is selected from toluene, xylene and combinations thereof.

19. The method according to claim 15 wherein said enamide has the formula:

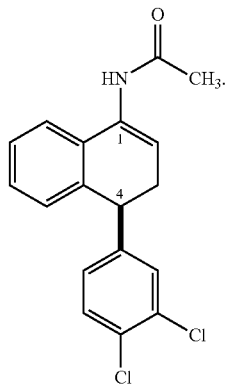

20. The method according to claim 19 wherein C-4 has a configuration selected from R, S and mixtures thereof.

21. The method according to claim 20 wherein C-4 is of S configuration.

22. The method according to claim 1, said method further comprising:
(b) contacting said enamide formed in step (a) with a hydrogenation catalyst and hydrogen or hydrogen transfer reagent under conditions appropriate to hydrogenate a carbon-carbon double bond of said enamide, thereby converting said enamide to an amide.

23. The method according to claim 22 wherein said catalyst is a chiral catalyst.

24. The method according to claim 23 wherein said chiral catalyst is a complex of a transition metal with a chiral phosphine ligand.

25. The method according to claim 22 wherein said amide is a racemic or chiral amide.

26. The method according to claim 22 wherein said amide has the formula:

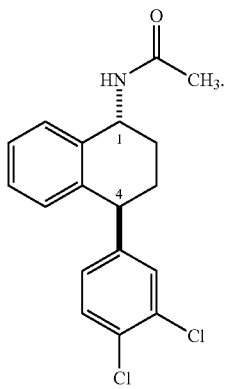

27. The method according to claim 26 wherein C-1 and C-4 have a configuration independently selected from R and S.

28. The method according to claim 27 wherein
C-1 is of R configuration; and
C-4 is of S configuration.

29. The method according to claim 22, further comprising:
(c) contacting said amide with a deacylating reagent under conditions appropriate to deacylate —HNC(O)R$^5$ of said amide, thereby forming an amine.

30. The method according to claim 29, further comprising:
(d) isolating said amine.

31. The method according to claim 30, wherein said isolating comprises selective crystallization.

32. The method according to claim 29 wherein said amine has the formula:

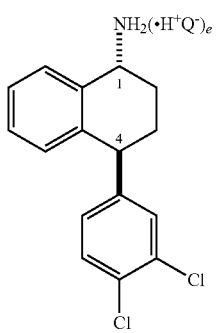

wherein
Q$^-$ is an anion; and
e is 0 to 1.

33. The method according to claim 32 wherein C-1 and C-4 have a configuration independently selected from R and S.

34. The method according to claim 33 wherein
C-1 is of R configuration; and
C-4 is of S configuration.

35. A method of converting an oxime having the formula

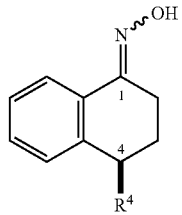

into an enamide having the formula:

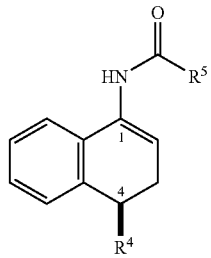

wherein
R$^4$ is selected from substituted or unsubstituted aryl and substituted or unsubstituted heteroaryl; and
R$^5$ is selected from H, substituted or unsubstituted alkyl, substituted or unsubstituted heteroalkyl, substituted or unsubstituted aryl, substituted or unsubstituted heteroaryl and substituted or unsubstituted heterocycloalkyl,
said method comprising:
(a) contacting said oxime with a phosphine and an acyl donor under conditions appropriate to convert said oxime to said enamide.

36. The method according to claim 35 wherein
C-4 is of S configuration.

37. The method according to claim 35 wherein said phosphine is a trialkylphosphine.

38. The method according to claim 35 wherein said oxime, said acyl donor and said phosphine are dissolved in an aromatic solvent.

39. The method according to claim 35 wherein said acyl donor is an alkyl anhydride.

40. The method according to claim 35, said method further comprising:
(b) contacting said enamide formed in step (a) with a chiral hydrogenation catalyst and hydrogen under conditions appropriate to hydrogenate a carbon-carbon double bond conjugated to C(O) of said enamide, thereby converting said enamide to an amide having the formula:

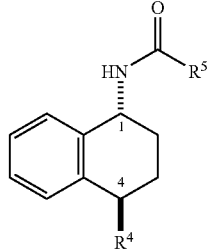

wherein
C-1 has a configuration selected from R and S.

41. The method according to claim 40 wherein said chiral catalyst comprises rhodium complexed to a chiral phosphine ligand.

42. The method according to claim 40, further comprising:

(c) contacting said amide with a deacylating reagent under conditions appropriate to deacylate —HNC(O)R⁵ of said amide, thereby forming an amine having the formula:

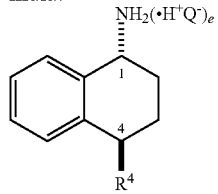

wherein

Q⁻ is an anion; and e is 0 or 1.

43. The method according to claim 42 wherein said deacylating reagent is an enzyme.

44. The method according to claim 42 wherein said deacylating reagent is an acid.

* * * * *

UNITED STATES PATENT AND TRADEMARK OFFICE
CERTIFICATE OF CORRECTION

| | | Page 1 of 1 |
|---|---|---|
| PATENT NO. | : 8,097,760 B2 | |
| APPLICATION NO. | : 12/281819 | |
| DATED | : January 17, 2012 | |
| INVENTOR(S) | : Zhao et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 371 days.

Signed and Sealed this
Seventeenth Day of April, 2012

David J. Kappos
*Director of the United States Patent and Trademark Office*